(12) United States Patent  
Chen

(10) Patent No.: US 11,414,676 B2  
(45) Date of Patent: Aug. 16, 2022

(54) AAV PRODUCTION IN INSECT CELLS, METHODS AND COMPOSITIONS THEREFOR

(71) Applicant: Virovek, Inc., Hayward, CA (US)

(72) Inventor: Haifeng Chen, Piedmont, CA (US)

(73) Assignee: Virovek, Inc., Hayward, CA (US)

( * ) Notice: Subject to any disclaimer, the term of this patent is extended or adjusted under 35 U.S.C. 154(b) by 0 days.

(21) Appl. No.: 16/112,149

(22) Filed: Aug. 24, 2018

(65) Prior Publication Data

US 2018/0371495 A1 Dec. 27, 2018

Related U.S. Application Data

(63) Continuation of application No. PCT/US2017/028660, filed on Apr. 20, 2017.

(Continued)

(51) Int. Cl.
*C12N 15/86* (2006.01)
*C07K 14/005* (2006.01)
*C12N 15/09* (2006.01)

(52) U.S. Cl.
CPC ............ *C12N 15/86* (2013.01); *C07K 14/005* (2013.01); *C12N 15/09* (2013.01);
(Continued)

(58) Field of Classification Search
None
See application file for complete search history.

(56) References Cited

U.S. PATENT DOCUMENTS 8,945,918 B2  2/2015  Chen
9,879,282 B2 *  1/2018  Chen ..................... C12N 7/00
(Continued)

FOREIGN PATENT DOCUMENTS

CN  1570121 A  1/2005
CN  101405033 A  4/2009
(Continued)

OTHER PUBLICATIONS

Pijlman et al. Evaluation of baculovirus expression vectors with enhanced stability in continuous cascaded insect-cell bioreactors. Biotechnol Bioeng. Sep. 20, 2004;87(6):743-53. (Year: 2004).*
Chen, H., et al., Baculoviral hr Sequences Increase Baculovirus Stability and AAV Production Yield. Molecular Therapy 25, 5S1, 2017.
(Continued)

*Primary Examiner* — Michelle S Horning
(74) *Attorney, Agent, or Firm* — Sandberg Phoenix & von Gontard P.C.

(57) ABSTRACT

Compositions and methods are disclosed for producing adeno-associated virus (AAV) in insect cells in vitro. Recombinant baculovirus vectors include an AAV Capsid gene expression cassette (Cap), an AAV Rep gene expression cassette (Rep), and a baculovirus homologous region (hr) located up to about 4 kb from a start codon in an AAV expression cassette. Production levels of baculovirus and AAV in insect cells harboring recombinant baculovirus comprising a Cap, a Rep, and an hr are higher compared to controls comprising a Cap and a Rep but no hr. Furthermore, levels of baculovirus and AAV production in insect cells infected with recombinant baculovirus comprising a Cap, a Rep, and an hr are comparatively stable over serial passages of cells, whereas levels of baculovirus and AAV production decline over serial passages of insect cells comprising recombinant baculovirus comprising a Cap and a Rep, but no hr.

12 Claims, 23 Drawing Sheets

Specification includes a Sequence Listing.

Related U.S. Application Data

(60) Provisional application No. 62/325,817, filed on Apr. 21, 2016.

(52) U.S. Cl.
CPC ............ *C12N 2710/14043* (2013.01); *C12N 2710/14044* (2013.01); *C12N 2710/14052* (2013.01); *C12N 2710/14121* (2013.01); *C12N 2710/14143* (2013.01); *C12N 2710/14144* (2013.01); *C12N 2750/14122* (2013.01); *C12N 2750/14143* (2013.01); *C12N 2750/14152* (2013.01)

(56) References Cited

U.S. PATENT DOCUMENTS

| | | |
|---|---|---|
| 2014/0186926 A1 | 7/2014 | Bakker |
| 2015/0140639 A1 | 5/2015 | Maria Christ Hermens et al. |
| 2018/0258448 A1 | 9/2018 | Hermens |

FOREIGN PATENT DOCUMENTS

| | | |
|---|---|---|
| CN | 101522903 A | 9/2009 |
| CN | 102007209 A | 4/2011 |
| WO | 2009014445 A2 | 1/2009 |
| WO | 2009104964 A1 | 8/2009 |
| WO | 2010114948 A3 | 5/2011 |

OTHER PUBLICATIONS

Lubelski, J., et al., Insect Cell-Based Recombinant Adeno-Associated Virus Production: Molecular Process Optimization. BioProcess J., 13(3): 6-, 2014.

Mietzsch, M., et al., OneBac 2.0: Sf9 Cell Lines for Production of AAV1, AAV2, and AAV8 Vectors with Minimal Encapsidation of Fore. Human Gene Therapy Methods 28, 15-22, 2017.

Mietzsch, M., et al. OneBac 2.0: Sf9 Cell Lines for Production of AAV5 Vectors with Enhanced Infectivity and Minimal Encapsidat. Human Gene Therapy Methods 26, 688-697, 2015.

Smith, R.H., et al., A Simplified Baculovirus-AAV Expression Vector System Coupled With One-step Affinity Purification Yields High-titer Molecular Therapy 17, 1888-1896, 2009.

Sokolenko, S., et al., Co-expression vs. co-infection using baculovirus expression vectors in insect cell culture: Benefits and drawb Biotechnology Advances 30, 766-781, 2012.

Aslanidi, G., et al., An inducible system for highly efficient production of recombinant adeno-associated virus (rAAV) vectors in insect Sf9 cells., Proc. Natl. Acad. Sci. USA, 106, 5059-5064, 2009.

Ayres, M.D., et al., The complete DNA sequence of Autographa californica nuclear polyhedrosis virus., Virology 202, 586-605, 1994.

Booth, M. J., et al., Transfection-free and scalable recombinant AAV vector production using HSV/AAV hybrids. Gene Ther., 11, 829-837, 2004.

Chen, H. Intron splicing-mediated expression of AAV Rep and Cap genes and production of AAV vectors in insect cells., Mol. Ther., 16, 924-930, 2008.

Chen, H. Exploiting the Intron-splicing Mechanism of Insect Cells to Produce Viral Vectors Harboring Toxic Genes for Suicide Gene Therapy., Mol. Ther. Nucleic Acids, 1, e57, 2012.

Cochran, M.A., and Faulkner, P., Location of Homologous DNA Sequences Interspersed at Five Regions in the Baculovirus AcMNPV Genome, J. Virol. 45, 3, 961-970, 1983.

Guarino, L.A. and Summers, M.D., Interspersed Homologous DNA of Autographa californica Nuclear Polyhedrosis Virus Enhances Delayed-Early Gene Expression, J. Virol., 60, 1, 215-223, 1986.

Guarino, L.A., et al., Complete Sequence and Enhancer Function of the Homologous DNA Regions of Autographa californica Nuclear Polyhedrosis Virus, J. Virol., 60, 1, 224-229, 1986.

Kohlbrenner, E., et al., Successful Production of Pseudotyped rAAV Vectors Using a Modified Baculovirus Expression System, Mol. Ther., 12, 6, 1217-1225, Dec. 2005.

Luckow, V., et al., Efficient generation of infectious recombinant baculoviruses by site-specific transposon-mediated insertion of foreign genes into a baculovirus genome propagated in *Escherichia coli.*, J. Virol., 67, 4566-4579, 1993.

Majima, K., et al., Divergence and Evolution of Homologous Regions of Bombyx mori Nuclear Polyhedrosis Virus, J. Virol. 67, 12, 7513-7521, 1993.

Pijman, G. P., et al., Evaluation of baculovirus expression vectors with enhanced stability in continuous cascaded insect-cell bioreactors., Biotechnol. Bioeng., 87, 743-753, 2004.

Tiwari, P., et al "Enhanced expression of recombinant proteins utilizing a modified baculovirus expression vector." Molecular biotechnology 46.1, 80-89, Apr. 28, 2010.

Urabe, M., et al., Insect Cells as a Factory to Produce Adeno-Assoicated Virus Type 2 Vectors, Human Gene Therapy 13, 1935-1943, 2001.

Xiao, X., et al., Production of high-titer recombinant adeno-associated virus vectors in the absence of helper adenovirus., J. Virol., 72, 2224-2232, 1998.

Young, S.M., et al., Roles of Adeno-Associated Virus Rep Protein and Human Chromosome 19 in Site-Specific Recombination, J. Virol., 74, 9, 3953-3966, 2000.

Grimm, D., et al., Novel Tools for Production and Purification of Recombinant Adenoassociated Virus Vectors, Human Gene Therapy, vol. 9, 1998, pp. 2745-2760.

Li, J., et al., Role for Highly Regulated rep Gene Expression in Adeno-Associated Virus Vector Production, J. Virol., vol. 71, 1997, pp. 5236-5243.

Chinese Search Report for 2017800100980 dated Oct. 28, 2021.

\* cited by examiner

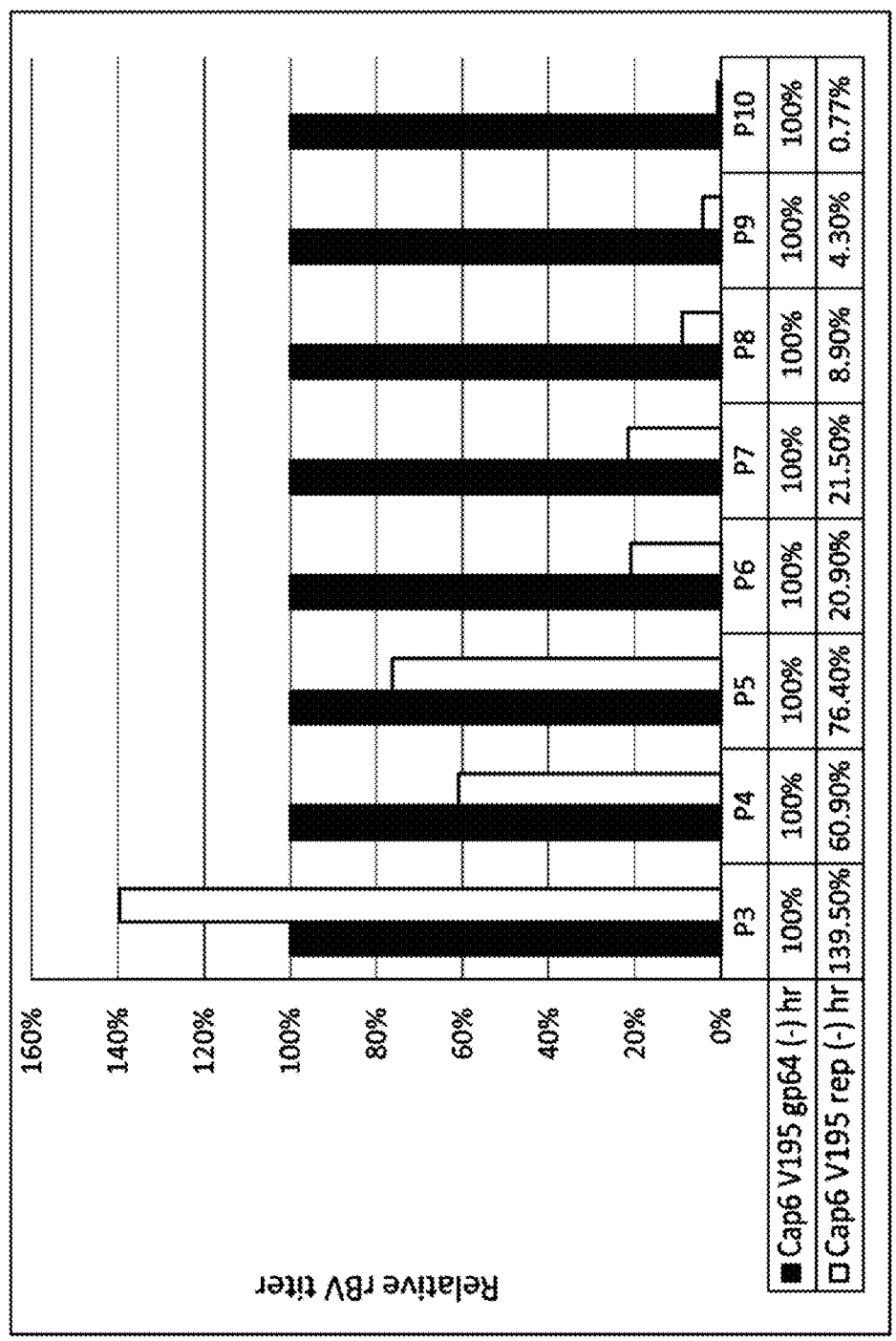

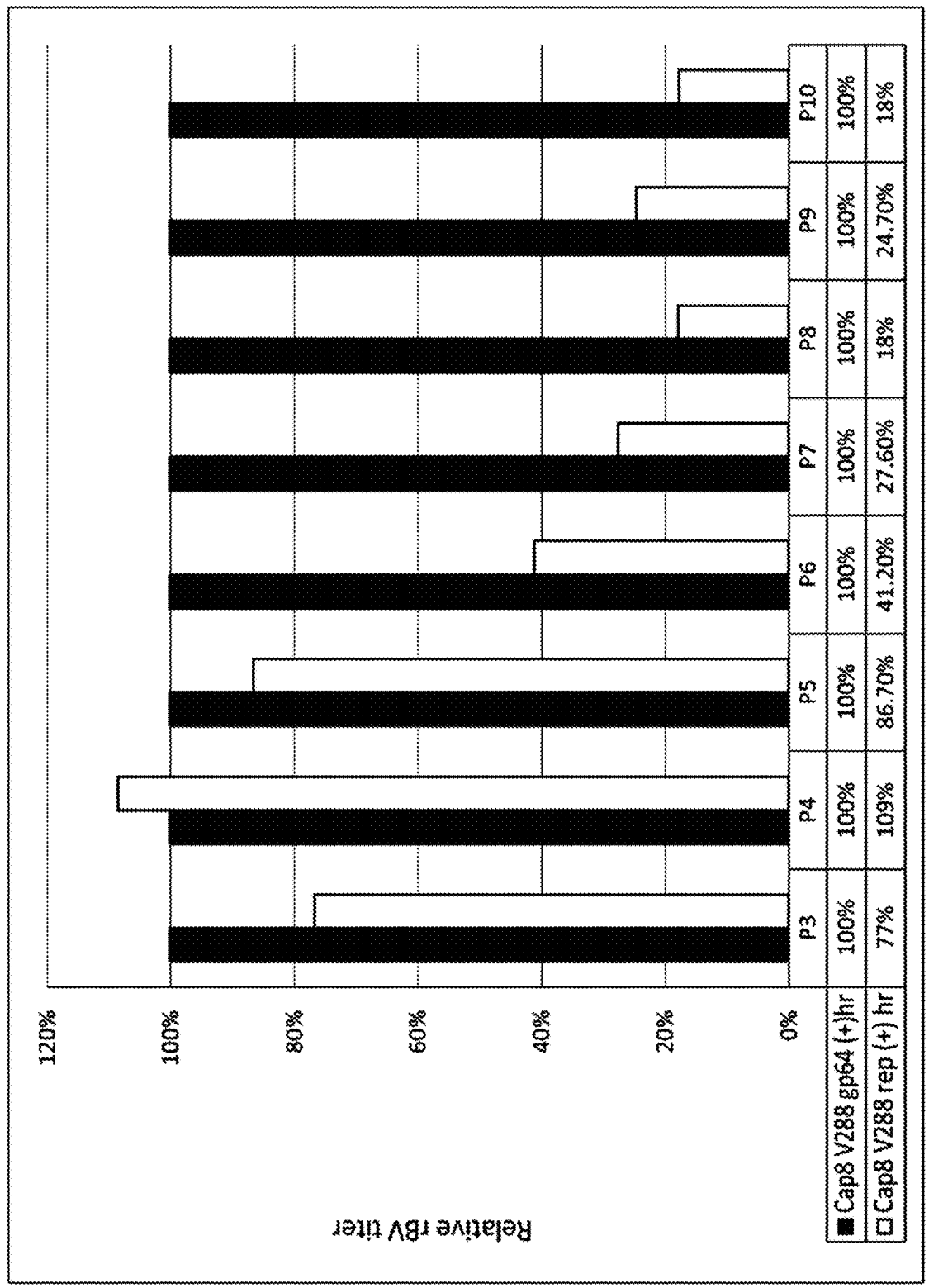

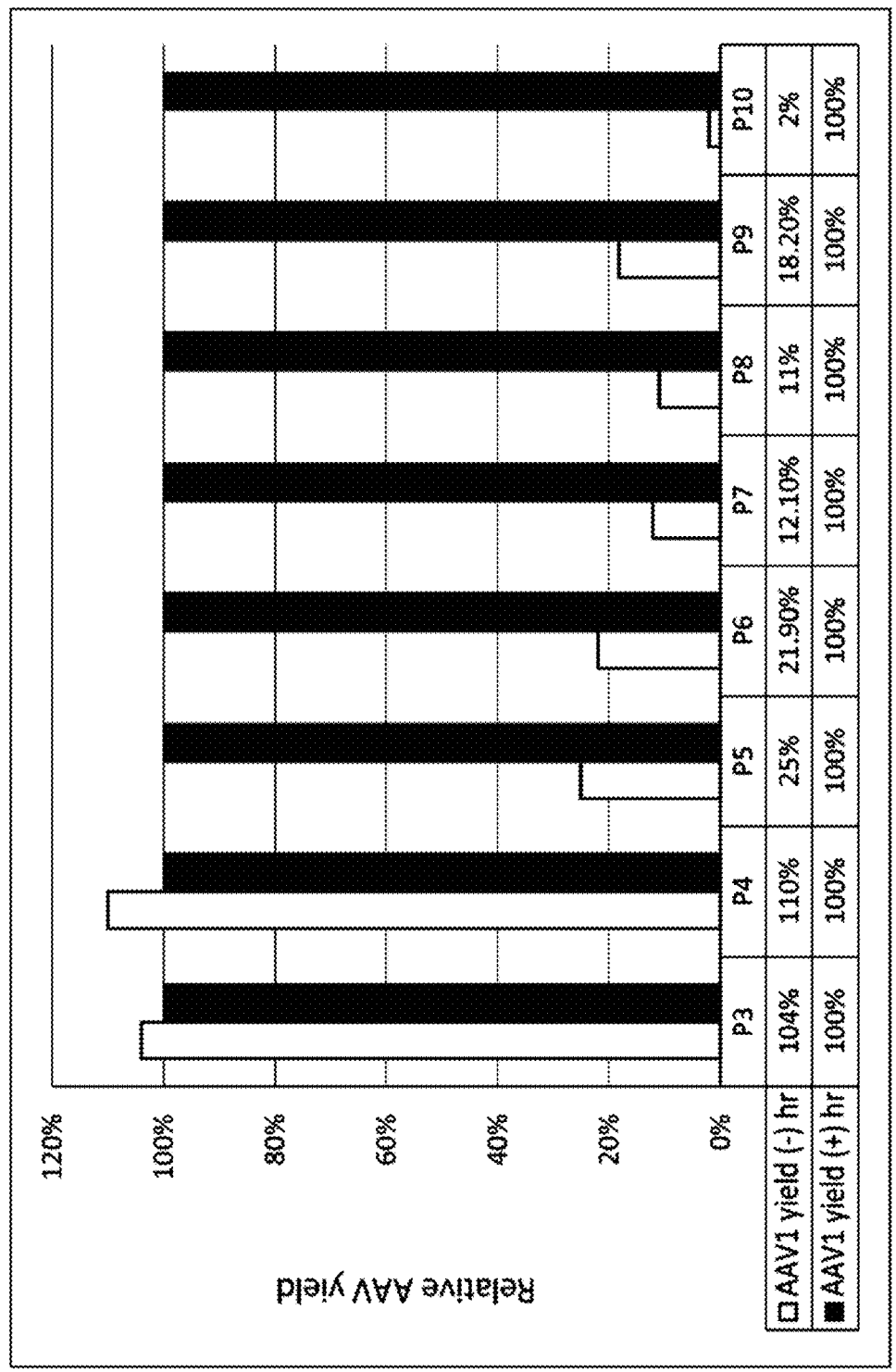

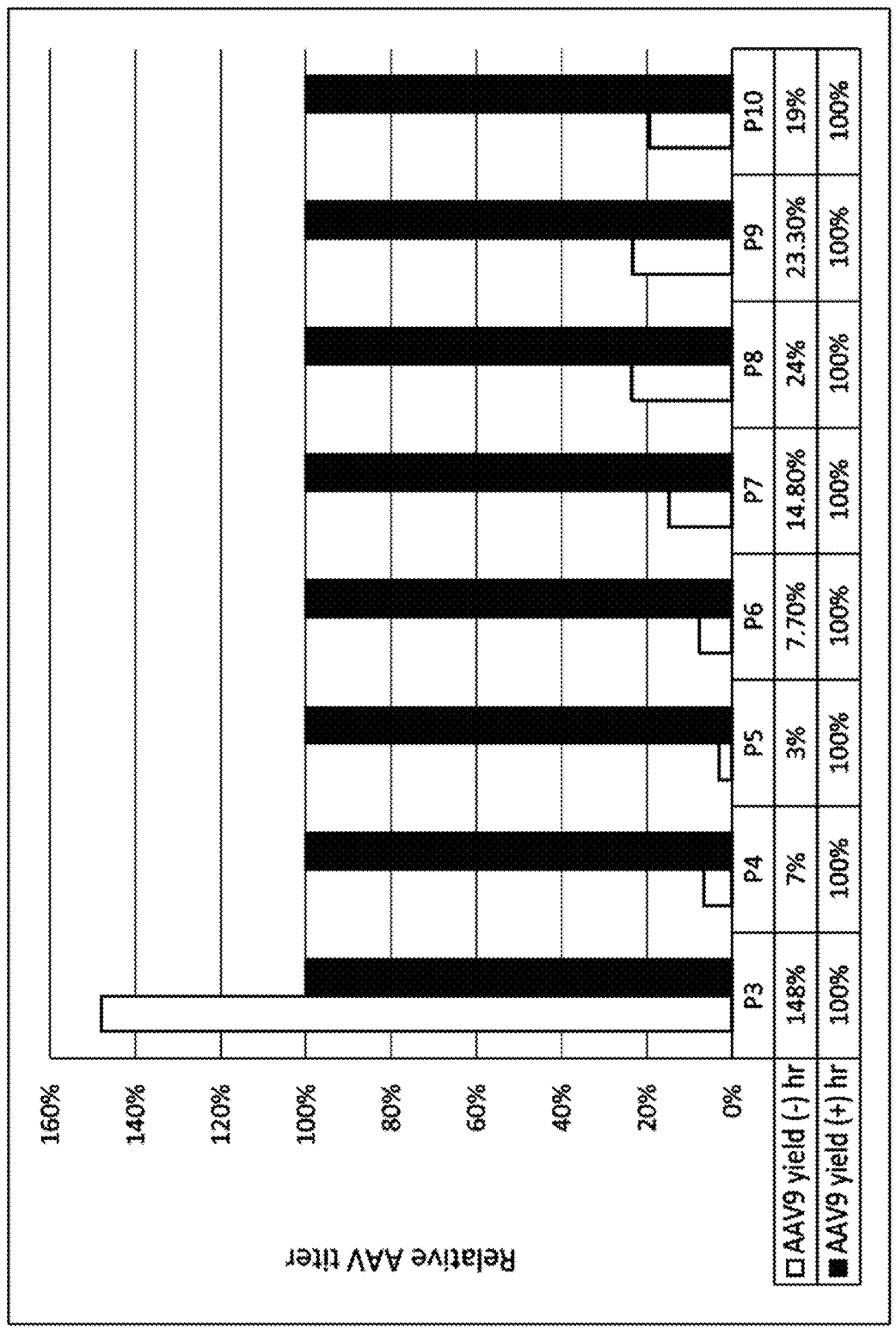

SEQUENCE LISTING

```
<160> NUMBER OF SEQ ID NOS: 14

<210> SEQ ID NO 1
<211> LENGTH: 880
<212> TYPE: DNA
<213> ORGANISM: Autographa californica nucleopolyhedrovirus

<400> SEQUENCE: 1
atcgatgatt gaccccaaca aaagatttat aattaatcat aatcacgaac aacaacaagt      60
caatgaaaca aataaacaag ttgtcgataa acattcata aatgacacag caacatacaa       120
ttcttgcata ataaaaattt aaatgacatc atatttgaga ataacaaatg acattatccc      180
tcgattgtgt tttacaagta gaattctacc cgtaaagcga gtttagtttt gaaaaacaaa      240
tgacatcatt tgtataatga catcatcccc tgattgtgtt ttacaagtag aattctatcc      300
gtaaagcgag ttcagttttg aaaacaaatg agtcatacct aaacacgtta ataatcttct      360
gatatcagct tatgactcaa gttatgagcc gtgtgcaaaa catgagataa gtttatgaca      420
tcatccactg atcgtgcgtt acaagtagaa ttctactcgt aaagccagtt cggttatgag      480
ccgtgtgcaa aacatgacat cagcttatga ctcatacttg attgtgtttt acgcgtagaa      540
ttctactcgt aaagcgagtt cggttatgag ccgtgtgcaa aacatgacat cagcttatga      600
gtcataatta atcgtgcgtt acaagtagaa ttctactcgt aaagcgagtt gaaggatcat      660
atttagttgc gtttatgaga taagattgaa aagcgtgtaa aatgtttccc gcgcttggca      720
caactattta caatgcggcc aagttataaa agattctaat ctgatatgtt ttaaaacacc      780
tttgcggccc gagttgtttg cgtacgtgac tagcgaagaa gatgtgtgga ccgcagaaca      840
gatagtaaaa caaaacccta gtattggagc aataatcgat                           880

<210> SEQ ID NO 2
<211> LENGTH: 990
<212> TYPE: DNA
<213> ORGANISM: Autographa californica nucleopolyhedrovirus
```

<400> SEQUENCE: 2

```
tgagcaaaac acaaccggca aattctcggc ggccgtttgg gaatgcggaa taattgccat      60
atgtaaatga tgtcatcggt tctaactcgc tttacgagta gaattctacg tgtaaaacat     120
aatcaagaga tgatgtcatt tgttttcaa aactgaactc aagaaatgat gtcatttgtt      180
tttcaaaact gaactggctt tacgagtaga attctacttg taaaacacaa tcgagagatg     240
atgtcatatt ttgcacacgg ctctaattaa actcgcttta cgagtaaaat tctacttgta     300
acgcatgatc aagggatgat gtcattggat gagtcatttg tttttcaaaa ctaaactcgc     360
tttacgagta gaattctact tgtaaaacac aatcaaggga tgatgtcatt atacaaatga     420
tgtcatttgt ttttcaaaac taaactcgct ttacggggtag aattctactt gtaaaacagc    480
aactcgaggg atgatgtcat cctttactcg atgattataa acgtgtttat gtatgactca     540
tttgttttc aaaactaaac tcgctttacg agtagaattc tacttgtaac gcacgatcaa      600
gggatgatgt catttatttg tgcaaagctc gatgtcatct tttgcacacg attataaaca     660
caatccaaat aatgactcat tgttttcaa aactgaactc gctttacgag tagaattcta      720
cttgtaaaac acaatcaagg gatgatgtca ttttcaaaat gatgtcattt gttttcaaa      780
actaaactcg ctttacgagt agaattctac ttgtaaaaca caatcaaggg atgatgtcat     840
tttaaaaatg atcatttgtt tttcaaaact aaactcgctt tacgagtaga attctacgtg     900
taaaacacaa tcaagggatg atgtcattta ctaaataaaa taattattta ataaaactg      960
tttttattg tcaaatacac attgattcac                                        990
```

<210> SEQ ID NO 3
<211> LENGTH: 684
<212> TYPE: DNA
<213> ORGANISM: Autographa californica nucleopolyhedrovirus

<400> SEQUENCE: 3

```
acgcgtagaa ttctacttgt aaagcaagtt aaaataagcc gtgtgcaaaa atgacatcag      60
acaaatgaca tcatctacct atcatgatca tgttaataat catgttttaa aatgacatca     120
gcttatgact aataattgat cgtgcgttac aagtagaatt ctactcgtaa agcgagttta     180
gttttgaaaa caaatgagtc atcattaaac atgttaataa tcgtgtataa aggatgacat     240
catccactaa tcgtgcgtta caagtagaat tctactcgta aagcgagttc ggttttgaaa     300
aacaaatgac atcatttctt gattgtgttt tacacgtaga attctactcg taaagtatgt     360
tcagtttaaa aacaaatga catcatttta cagatgacat catttcttga ttatgtttta     420
caagtagaat tctactcgta aagcgagttt agttttaaaa acaaatgac atcatctctt      480
gattatgttt tacaagtaga attctactcg taaagcgagt ttagttttga aaacaaatg     540
acatcatctc ttgattatgt tttacaagta gaattctact cgtaaagcga gtttagttttt    600
gaaaaacaaa tgacatcatc ccttgatcat gcgttacaag tagaattcta ctcgtaaagc     660
gagttgaatt ttgattacaa tatt                                           684
```

<210> SEQ ID NO 4
<211> LENGTH: 675
<212> TYPE: DNA
<213> ORGANISM: Autographa californica nucleopolyhedrovirus

<400> SEQUENCE: 4

```
atgcatataa ttgtgtacaa aatatgactc attaatcgat cgtgcgttac aagtagaatt      60
ctactggtaa agcaagttcg gttgtgagcc gtgtgcaaaa catgacatca taactaatca     120
tgtttataat catgtgcaaa atatgacatc atccgacgat tgtgttttac aagtagaatt     180
ctactcgtaa agcgagttta aaaattttgt gacgtcaatg aaacaacgtg taatattttt     240
tacaatattt aagtgaaaca ttatgacttc caataatttt gtggatgtgg atacgtttgc     300
aagacaattg attacagata aatgtagtgc tctaatcgaa agatgcggat ctgttgccgg     360
caaacatttt agagattagt agagaaaggc cagagacaag tattttgagg tgccaactca     420
aaaaaactat gaatacatta aaaaattatt tttacgaaca aaatatatgg acgattcgat     480
agattataaa gattttaaca gacgcatcct attgatagtt tttaaattcg ctttaaacaa     540
gagcaccaac tactttccat cgtactaaag agatcatcga ggtggccatt aaacgtttaa     600
acaaaattaa ccccgattta aagagttctc cgcgcaatgc ttcagcatta caaatgaatg     660
tttggaaaat ctaga                                                      675
```

<210> SEQ ID NO 5
<211> LENGTH: 418
<212> TYPE: DNA
<213> ORGANISM: Autographa californica nucleopolyhedrovirus

<400> SEQUENCE: 5

```
aactggcttt acgagtagaa ttctacttgt aaaacacaat caagaaatga tgtcattttt      60
gtacgtgatt ataaacatgt ttaaacatgg tacattgaac ttaatttttg caagttgata     120
aactagatta atgtatgact catttgtttg tgcaagttga taaacgtgat taatatatga     180
ctcatatgtt tgtgcaaaaa tggtgtcatc gtacaaactc gctttacgag tagaattcta     240
cttgtaaaac acaatcgagg gatgatgtca tttgtagaat gatgtcattt gttttttcaa     300
aaccgaactc gctttacgag tagaattcta cttgtaaaac acaatcgagg gatgatgtca     360
tttgtagaat gatgtcatcg tacaaactcg ctttacgagt agaattctag taaaacac       418
```

<210> SEQ ID NO 6
<211> LENGTH: 725
<212> TYPE: DNA
<213> ORGANISM: Autographa californica nucleopolyhedrovirus

<400> SEQUENCE: 6

```
ttgaaaattt attgcctaat attattttg tcagttcgtt gtcatttatt aatttggatg        60
atgtccattt gttttaaaa ttgaactggc tttacgagta gaattctacg cgtaaaacac       120
aatcaagtat gagtcataag ctgatgtcat gttttgcaca cggctcataa ccgaactggc      180
tttacgagta gaattctact tgtaacgcac gatcgagtgg atgatggtca tttgttttc       240
aaatcgagat gatgtcatgt tttgcacacg ggctcataaa ctgctttacg agtagaattc      300
tacgtgtaac gcacgatcga ttgatgagtc atttgttttg caatatgata tcatacaata      360
tgactcattt gttttttcaaa accgaacttg atttacgggt agaattctac tcgtaaagca      420
caatcaaaaa gatgatgtca tttgtttttc aaaactgaac tctcggcttt acgagtagaa      480
ttctacgtgt aaaacacaat caagaaatga tgtcatttgt tataaaaata aaagctgatg      540
tcatgttttg cacatggctc ataactaaac tcgctttacg ggtagaattc tacgcgtaaa      600
acatgattga taattaaata attcatttgc aaagctatac gttaaatcaa acggacgtta      660
```

```
tggaattgta taatattaaa tatgcaattg atccaacaaa taaaattata atagagcaag    720
tcgac                                                                725
```

```
<210> SEQ ID NO 7
<211> LENGTH: 25
<212> TYPE: DNA
<213> ORGANISM: Artificial Sequence
<220> FEATURE:
<223> OTHER INFORMATION: PCR primer

<400> SEQUENCE: 7
gctttacgag tagaattcta cgtgt                                          25

<210> SEQ ID NO 8
<211> LENGTH: 35
<212> TYPE: DNA
<213> ORGANISM: Artificial Sequence
<220> FEATURE:
<223> OTHER INFORMATION: cloning pcr primer

<400> SEQUENCE: 8
ggcctacgta gttttacacg tagaattcta ctcgt                               35

<210> SEQ ID NO 9
<211> LENGTH: 20
<212> TYPE: DNA
<213> ORGANISM: Artificial Sequence
<220> FEATURE:
<223> OTHER INFORMATION: cloning PCR primer

<400> SEQUENCE: 9
atttgacttg gtcagggccg                                                20

<210> SEQ ID NO 10
<211> LENGTH: 40
<212> TYPE: DNA
<213> ORGANISM: Artificial Sequence
<220> FEATURE:
<223> OTHER INFORMATION: cloning/pcr primer

<400> SEQUENCE: 10
gaattctact cgtaaagccc agttgacata agcctgttcg                          40

<210> SEQ ID NO 11
<211> LENGTH: 24
<212> TYPE: DNA
<213> ORGANISM: Artificial Sequence
<220> FEATURE:
<223> OTHER INFORMATION: qPCR Primer

<400> SEQUENCE: 11
ccctctgtgt acttggctct aacg                                           24

<210> SEQ ID NO 12
<211> LENGTH: 25
<212> TYPE: DNA
<213> ORGANISM: Artificial Sequence
<220> FEATURE:
<223> OTHER INFORMATION: qPCR primer

<400> SEQUENCE: 12
cggtgaaacg caaagtcgag caccg                                          25

<210> SEQ ID NO 13
<211> LENGTH: 20
```

```
<212> TYPE: DNA
<213> ORGANISM: Artificial Sequence
<220> FEATURE:
<223> OTHER INFORMATION: qPCR primer

<400> SEQUENCE: 13
attcatgctc cacctcaacc                                              20

<210> SEQ ID NO 14
<211> LENGTH: 20
<212> TYPE: DNA
<213> ORGANISM: Artificial Sequence
<220> FEATURE:
<223> OTHER INFORMATION: qPCR sequence

<400> SEQUENCE: 14
gccgtctgga tcatgacttt                                              20
```

AAV PRODUCTION IN INSECT CELLS, METHODS AND COMPOSITIONS THEREFOR

REFERENCE TO PRIOR APPLICATION

This application is a Continuation of and claims benefit of priority to PCT/US17/28660 filed on Apr. 20, 2017, which claims benefit of priority to U.S. Provisional Application 62/325,817 filed Apr. 21, 2016. Application 62/325,817 and PCT/US17/28660 are hereby incorporated by reference each in its entirety.

INCORPORATION BY REFERENCE OF SEQUENCE LISTING

The Sequence Listing, which is a part of the present disclosure, includes a computer readable form and a written sequence listing comprising nucleotide and/or amino acid sequences. The sequence listing information recorded in computer readable form is identical to the written sequence listing. The subject matter of the Sequence Listing is incorporated herein by reference in its entirety

INTRODUCTION

With the approval of the first adeno-associated virus (AAV)-mediated gene therapy drug, the demand for large scale AAV vector manufacturing technology is ever increasing (Ylä-Herttuala, S., Mol. Ther. 20, 1831-1832, 2012). Currently there are several technologies for producing AAV. The traditional method utilizes transfection of HEK293 cells or other mammalian cell lines with triple or double plasmids. This method has low yields of AAV and is difficult to scale up due to its requirement for adherent cells (Xiao, X., Li, J. & Samulski, R. J., J. Virol. 72, 2224-2232, 1998). Another method for producing AAV utilizes Herpes Simplex virus (HSV) to infect mammalian cells. This method is hampered by difficulties in generating sufficient HSV seed stocks, and also has low AAV productivity (Booth, M. J., et al., Gene Ther. 11, 829-837, 2004).

Baculovirus-based methods for AAV vector production in insect cells have significantly increased AAV production yields compared to other systems (Urabe, M., et al., Human Gene Therapy 13, 1935-1943, 2001; Chen, H., Mol. Ther. 16, 924-930, 2008; Chen, H., Molecular Therapy-Nucleic Acids 1, e57, 2012; U.S. Pat. No. 8,945,918 to Chen). However, recombinant baculovirus can be unstable over multiple passages, leading to a decline in AAV production. There is thus an unmet need for an AAV production system that can maintain production of AAV vectors at a high yield even after multiple passages.

The baculovirus *Autographa californica* multiple nuclear polyhedrosis virus (AcMNPV) genome includes 5 "homologous regions" (hrs) designated hr1-hr5 (Cochran, M. A., and Faulkner, P., J. Virol. 45, %1-970, 1983; Guarino, L. A. and Summers, M. D., J. Virol. 60, 214-223, 1986). These 5 regions can function as enhancers (Guarino, L. A., et al., J. Virol. 60, 224-229, 1986). Sequences of hr1-hr5 have been reported (Guarino, L. A. and Summers, M. D., J. Virol. 60,214-223, 1986; Guarino, L. A., et al., J. Virol. 60,224-229, 1986) and are set forth herein. An hr can be from about 400 base pairs up to about 1,000 base pairs in length. Examples of sequences of AcMNPV hrs are as follows.

```
hr1: ATCGATGATT GACCCCAACA AAAGATTTAT AATTAATCAT

AATCACGAAC AACAACAAGT CAATGAAACA AATAAACAAG TTGTCGATAA

AACATTCATA AATGACACAG CAACATACAA TTCTTGCATA ATAAAAATTT

AAATGACATC ATATTTGAGA ATAACAAATG ACATTATCCC TCGATTGTGT

TTTACAAGTA GAATTCTACC CGTAAAGCGA GTTTAGTTTT GAAAAACAAA

TGACATCATT TGTATAATGA CATCATCCCC TGATTGTGTT TTACAAGTAG

AATTCTATCC GTAAAGCGAG TTCAGTTTTG AAAACAAATG AGTCATACCT

AAACACGTTA ATAATCTTCT GATATCAGCT TATGACTCAA GTTATGAGCC

GTGTGCAAAA CATGAGATAA GTTTATGACA TCATCCACTG ATCGTGCGTT

ACAAGTAGAA TTCTACTCGT AAAGCCAGTT CGGTTATGAG CCGTGTGCAA

AACATGACAT CAGCTTATGA CTCATACTTG ATTGTGTTTT ACGCGTAGAA

TTCTACTCGT AAAGCGAGTT CGGTTATGAG CCGTGTGCAA AACATGACAT

CAGCTTATGA GTCATAATTA ATCGTGCGTT ACAAGTAGAA TTCTACTCGT

AAAGCGAGTT GAAGGATCAT ATTTAGTTGC GTTTATGAGA TAAGATTGAA

AAGCGTGTAA AATGTTTCCC GCGCTTGGCA CAACTATTTA CAATGCGGCC

AAGTTATAAA AGATTCTAAT CTGATATGTT TTAAAACACC TTTGCGGCCC

GAGTTGTTTG CGTACGTGAC TAGCGAAGAA GATGTGTGGA CCGCAGAACA

GATAGTAAAA CAAAACCCTA GTATTGGAGC AATAATCGAT (SEQ ID NO: 1)

hr2: TGAGCAAAAC ACAACCGGCA AATTCTCGGC GGCCGTTTGG

GAATGCGGAA TAATTGCCAT ATGTAAATGA TGTCATCGGT TCTAACTCGC
```

-continued

TTTACGAGTA GAATTCTACG TGTAAAACAT AATCAAGAGA TGATGTCATT

TGTTTTTCAA AACTGAACTC AAGAAATGAT GTCATTTGTT TTTCAAAACT

GAACTGGCTT TACGAGTAGA ATTCTACTTG TAAAACACAA TCGAGAGATG

ATGTCATATT TTGCACACGG CTCTAATTAA ACTCGCTTTA CGAGTAAAAT

TCTACTTGTA ACGCATGATC AAGGGATGAT GTCATTGGAT GAGTCATTTG

TTTTTCAAAA CTAAACTCGC TTTACGAGTA GAATTCTACT TGTAAAACAC

AATCAAGGGA TGATGTCATT ATACAAATGA TGTCATTTGT TTTTCAAAAC

TAAACTCGCT TTACGGGTAG AATTCTACTT GTAAAACAGC AACTCGAGGG

ATGATGTCAT CCTTTACTCG ATGATTATAA ACGTGTTTAT GTATGACTCA

TTTGTTTTTC AAAACTAAAC TCGCTTTACG AGTAGAATTC TACTTGTAAC

GCACGATCAA GGGATGATGT CATTTATTTG TGCAAAGCTC GATGTCATCT

TTTGCACACG ATTATAAACA CAATCCAAAT AATGACTCAT TTGTTTTCAA

AACTGAACTC GCTTTACGAG TAGAATTCTA CTTGTAAAAC ACAATCAAGG

GATGATGTCA TTTTCAAAAT GATGTCATTT GTTTTTCAAA ACTAAACTCG

CTTTACGAGT AGAATTCTAC TTGTAAAACA CAATCAAGGG ATGATGTCAT

TTTAAAAATG ATCATTTGTT TTTCAAAACT AAACTCGCTT TACGAGTAGA

ATTCTACGTG TAAAACACAA TCAAGGGATG ATGTCATTTA CTAAATAAAA

TAATTATTTA AATAAAACTG TTTTTTATTG TCAAATACAC ATTGATTCAC (SEQ

ID NO: 2)

hr3: ACGCGTAGAA TTCTACTTGT AAAGCAAGTT AAAATAAGCC

GTGTGCAAAA ATGACATCAG ACAAATGACA TCATCTACCT ATCATGATCA

TGTTAATAAT CATGTTTTAA AATGACATCA GCTTATGACT AATAATTGAT

CGTGCGTTAC AAGTAGAATT CTACTCGTAA AGCGAGTTTA GTTTTGAAAA

CAAATGAGTC ATCATTAAAC ATGTTAATAA TCGTGTATAA AGGATGACAT

CATCCACTAA TCGTGCGTTA CAAGTAGAAT TCTACTCGTA AAGCGAGTTC

GGTTTTGAAA AACAAATGAC ATCATTTCTT GATTGTGTTT TACACGTAGA

ATTCTACTCG TAAAGTATGT TCAGTTTAAA AACAAATGA CATCATTTTA

CAGATGACAT CATTTCTTGA TTATGTTTTA CAAGTAGAAT TCTACTCGTA

AAGCGAGTTT AGTTTAAAA AACAAATGAC ATCATCTCTT GATTATGTTT

TACAAGTAGA ATTCTACTCG TAAAGCGAGT TTAGTTTTGA AAACAAATG

ACATCATCTC TTGATTATGT TTTACAAGTA GAATTCTACT CGTAAAGCGA

GTTTAGTTTT GAAAACAAA TGACATCATC CCTTGATCAT GCGTTACAAG

TAGAATTCTA CTCGTAAAGC GAGTTGAATT TGATTACAA TATT (SEQ ID NO: 3)

hr4 left: ATGCATATAA TTGTGTACAA AATATGACTC ATTAATCGAT

CGTGCGTTAC AAGTAGAATT CTACTGGTAA AGCAAGTTCG GTTGTGAGCC

GTGTGCAAAA CATGACATCA TAACTAATCA TGTTTATAAT CATGTGCAAA

ATATGACATC ATCCGACGAT TGTGTTTTAC AAGTAGAATT CTACTCGTAA

AGCGAGTTTA AAAATTTGT GACGTCAATG AAACAACGTG TAATATTTTT

TACAATATTT AAGTGAAACA TTATGACTTC AATAATTTT GTGGATGTGG

ATACGTTTGC AAGACAATTG ATTACAGATA AATGTAGTGC TCTAATCGAA

AGATGCGGAT CTGTTGCCGG CAAACATTTT AGAGATTAGT AGAGAAAGGC

-continued

```
CAGAGACAAG TATTTTGAGG TGCCAACTCA AAAAAACTAT GAATACATTA

AAAAATTATT TTTACGAACA AAATATATGG ACGATTCGAT AGATTATAAA

GATTTTAACA GACGCATCCT ATTGATAGTT TTTAAATTCG CTTTAAACAA

GAGCACCAAC TACTTTCCAT CGTACTAAAG AGATCATCGA GGTGGCCATT

AAACGTTTAA ACAAAATTAA CCCCGATTTA AAGAGTTCTC CGCGCAATGC

TTCAGCATTA CAAATGAATG TTTGGAAAAT CTAGA (SEQ ID NO: 4)

hr4 right: AACTGGCTTT ACGAGTAGAA TTCTACTTGT AAAACACAAT

CAAGAAATGA TGTCATTTTT GTACGTGATT ATAAACATGT TTAAACATGG

TACATTGAAC TTAATTTTTG CAAGTTGATA AACTAGATTA ATGTATGACT

CATTTGTTTG TGCAAGTTGA TAAACGTGAT TAATATATGA CTCATATGTT

TGTGCAAAAA TGGTGTCATC GTACAAACTC GCTTTACGAG TAGAATTCTA

CTTGTAAAAC ACAATCGAGG GATGATGTCA TTTGTAGAAT GATGTCATTT

GTTTTTTCAA AACCGAACTC GCTTTACGAG TAGAATTCTA CTTGTAAAAC

ACAATCGAGG GATGATGTCA TTTGTAGAAT GATGTCATCG TACAAACTCG

CTTTACGAGT AGAATTCTAG TAAAACAC (SEQ ID NO: 5)

hr5: TTGAAAATTT ATTGCCTAAT ATTATTTTTG TCAGTTCGTT

GTCATTTATT AATTTGGATG ATGTCCATTT GTTTTTAAAA TTGAACTGGC

TTTACGAGTA GAATTCTACG CGTAAAACAC AATCAAGTAT GAGTCATAAG

CTGATGTCAT GTTTTGCACA CGGCTCATAA CCGAACTGGC TTTACGAGTA

GAATTCTACT TGTAACGCAC GATCGAGTGG ATGATGGTCA TTTGTTTTTC

AAATCGAGAT GATGTCATGT TTTGCACACG GGCTCATAAA CTGCTTTACG

AGTAGAATTC TACGTGTAAC GCACGATCGA TTGATGAGTC ATTTGTTTTG

CAATATGATA TCATACAATA TGACTCATTT GTTTTTCAAA ACCGAACTTG

ATTTACGGGT AGAATTCTAC TCGTAAAGCA CAATCAAAAA GATGATGTCA

TTTGTTTTTC AAAACTGAAC TCTCGGCTTT ACGAGTAGAA TTCTACGTGT

AAAACACAAT CAAGAAATGA TGTCATTTGT TATAAAAATA AAAGCTGATG

TCATGTTTTG CACATGGCTC ATAACTAAAC TCGCTTTACG GGTAGAATTC

TACGCGTAAA ACATGATTGA TAATTAAATA ATTCATTTGC AAAGCTATAC

GTTAAATCAA ACGGACGTTA TGGAATTGTA TAATATTAAA TATGCAATTG

ATCCAACAAA TAAAATTATA ATAGAGCAAG TCGAC (SEQ ID NO: 6)
``` hr1-hr4 sequences are from Guarino, L. A., et al., J. Virol. 60, 224-229, 1986. hr5 sequence is from Guarino, L. A. and Summers, M. D., J. Virol. 60, 214-223, 1986. Other sequences for hr2 are reported in Aslanidi, G., et al., Proc. Nat'l. Acad. Sci. USA 106, 5059-5064, 2009, and Ayres, M. D., et al., Virology 202, 586-605, 1994.

In addition, sequence diversity amongst hrs in insect viruses has been reported. Sequences with as little as 64% identity with an AcMNPV hr have been recognized as hr sequences from *Bombyx mori* Nuclear Polyhedrosis Virus (Majima, K., et al., J. Virol. 67, 7513-7521, 1993).

It has been reported that baculovirus hrs can act through an AAV2 cis-acting Rep-Binding Element (RBE) to enhance AAV production in an insect cell line that harbors AAV Rep and Cap genes (Aslanidi, G., et al., Proc. Nat'l. Acad. Sci. USA 106, 5059-5064, 2009). This study tested expression of AAV rep genes in a transient transfection assay, and reported elevated transcription upon transfection with a construct harboring hr2 and an RBE upstream to rep. The investigators proposed a feed-forward loop, in which transcription of both the AAV rep and cap genes is induced by trans-acting baculovirus expression vector-encoded immediate-early trans-regulator 1 (IE-1). In their model, one of the products (a Rep protein) interacts with the RBE to induce rescue/amplification and mediate more transcription.

Baculovirus hr sequences have also been reported to stabilize recombinant baculoviruses in continuous-cascade insect-cell bioreactors (Pijlman, G. P., et al., Biotechnol. Bioeng. 87, 743-753, 2004). However, there has been no report of an hr sequence enhancing AAV virus productivity in a baculovirus system.

SUMMARY

The present inventor has developed compositions and methods for enhancing adeno-associated virus (AAV) production in baculovirus-based systems in insect cells in vitro. The compositions and methods employ vectors that do not have a AAV Rep-binding element (RBE) but include a baculovirus homologous region (hr). In various configurations, stability of an insect cell line harboring a baculovirus genome which includes an AAV genome can be maintained over multiple passages.

In various configurations, AAV production in insect cells comprising a vector of the present teachings can be enhanced compared to vectors that do not include an hr. Furthermore, insect cell lines comprising a vector of the present teachings can stably maintain high titers of AAV production even after repeated passages.

In various embodiments, the present teachings include vectors. In various configurations, a vector can be a baculovirus or a plasmid, such as, for example but without limitation, a bacmid shuttle vector (Luckow, V., et al., J. Virol. 67, 4566-4579, 1993). In various configurations, a vector can comprise an AAV Cap expression cassette, an AAV Rep expression cassette, and a baculovirus homologous region (hr). In various configurations, the hr can be located up to about 4 kb from a start codon of an AAV expression cassette. In various configurations, the hr can be an insertion. In various configurations, the hr can be located up to about 0.5 kb, about 1 kb, about 1.5 kb, about 2 kb, about 2.5 kb, about 3 kb, about 3.5 kb, about 4 kb or about 4.5 kb from the start codon of an AAV expression cassette. In various configurations, an inserted hr region can be located up to about 4 kb from a start codon of Rep expression cassette. In various configurations, an inserted hr region can be located up to about 4 kb from a start codon of Cap expression cassette. In various configurations, a vector can include sequences from a virus such as a baculovirus, such as, without limitation, an *Autographa californica* Multiple Nuclear Polyhedrosis Virus (AcMNPV). In some configurations, a vector can be vector described previously (Chen, H., Mol. Ther. 16, 924-930, 2008; Chen, H., Molecular Therapy-Nucleic Acids 1, e57, 2012; U.S. Pat. No. 8,945,918 to Chen) modified to include an hr.

In various configurations, the AAV Cap expression cassette and the AAV Rep expression cassette can be as described previously (Chen, H., Mol. Ther. 16, 924-930, 2008; Chen, H., Molecular Therapy-Nucleic Acids 1, e57, 2012; U.S. Pat. No. 8,945,918 to Chen), and the hr can be an hr1, an hr2, an hr3, an hr4 or an hr5 from a baculovirus such as AcMNPV. In some configurations, the hr can be an AcMNPV hr2. In some configurations, an hr can be an hr sharing sequence identity with an AcMNPV hr, and can be, for example and without limitation, an hr from an AcMNPV, an hr from another insect virus, or an artificial hr sequence sharing at least 64% sequence identity, at least 65% sequence identity, at least 70% sequence identity, at least 75% sequence identity, at least 80% sequence identity, at least 85% sequence identity, at least 90% sequence identity, at least 95% sequence identity, or greater sequence identity with an AcMNPV hr such as hr2.

In various configurations, a vector of the present teachings can exclude a Rep Binding Element (RBE), and AAV can be produced in insect cells at using vectors that comprise an hr but do not comprise an RBE.

In various configurations, a vector of the present teachings can comprise, in 5' to 3' order, a Cap expression cassette, a Rep expression cassette, and a baculovirus homologous region.

In various configurations, a vector of the present teachings can comprise, in 5' to 3' order, a Rep expression cassette, a Cap expression cassette, and a baculovirus homologous region.

In various configurations, a vector of the present teachings can comprise, in 5' to 3' order, a Cap expression cassette, a baculovirus homologous region, and a Rep expression cassette.

In various configurations, a vector of the present teachings can comprise, in 5' to 3' order, a Rep expression cassette, a baculovirus homologous region, and a Cap expression cassette.

In various configurations, a vector of the present teachings can comprise, in 5' to 3' order, a baculovirus homologous region, a Cap expression cassette, and a Rep expression cassette.

In various configurations, a vector of the present teachings can comprise, in 5' to 3' order, a baculovirus homologous region, a Rep expression cassette, and a Cap expression cassette.

In various configurations, the hr region can be located between the Rep expression cassette and the Cap expression cassette. In various configurations, the Rep expression cassette and the Cap expression cassette can be in a head-to-head (5' to 5') orientation, a tail-to-tail (3' to 3') orientation, or a head-to-tail (5' to 3') orientation.

In various configurations, the present teachings include insect cell lines, such as, for example and without limitation, Sf9 cells, Tni Pro cells, or E4a cells that comprise a vector described herein. In various configurations, the present teachings include insect cell lines, such as and without limitation, Sf9 cells.

In some embodiments, the present teachings include methods of growing baculovirus in vitro. In various configurations, these methods include providing a culture of insect cells, infecting or transfecting the insect cells with a vector comprising an AAV Cap expression cassette, an AAV Rep expression cassette, and a baculovirus homologous region (hr), and incubating the cells. In various configurations, the hr can be up to about 4 kb from an AAV expression cassette. In various configurations, the hr can be up to about 4 kb from a Rep expression cassette. In various configurations, the hr can be up to about 4 kb from a Cap expression cassette. In various aspects, resulting cell lines can be repeatedly passaged.

In some embodiments, the present teachings include methods of growing AAV in vitro. In these methods, a baculovirus comprising an AAV Cap cassette, an AAV Rep cassette and an hr can be used to infect or transfect (or co-infect or co-transfect) an insect cell such as, for example and without limitation, an Sf9 cell, a Tni Pro cell, or an E4a cell. An infected (or transfected) cell can then be grown in vitro and thereby form a cell line that produces baculovirus and AAV. Such cell lines can be repeatedly passaged for multiple passages with little or no loss of AAV production, for example for at least 3 passages, at least 4 passages, at least 5 passages, at least 6 passages, at least 7 passages, at least 8 passages, at least 9 passages, or at least 10 passages. In various configurations, AAV production from an insect cell line comprising a vector comprising an AAV Cap expression cassette, an AAV Rep expression cassette and an hr of the present teachings can be, e.g., after 7 passages, at least 2-fold greater, at least 3-fold greater, or at least 4-fold greater than that of an insect cell line comprising a vector comprising an AAV Cap expression cassette and an AAV Rep expression cassette but no hr after 7 passages. In various configurations, AAV production from an insect cell line comprising a vector comprising an AAV Cap expression cassette, an AAV Rep expression cassette and an hr of the present teachings can be, e.g., after 8 passages, at least 2-fold greater, at least 3-fold greater, or at least 4-fold greater than that of an insect cell line comprising a vector comprising an AAV Cap expression cassette and an AAV Rep expression cassette but no hr after 8 passages. In various configurations, AAV production from an insect cell line comprising a vector comprising an AAV Cap expression cassette, an AAV Rep expression cassette and an hr of the present teachings can be, e.g., after 9 passages, at least 2-fold greater, at least 3-fold greater, or at least 4-fold greater than that of an insect cell line comprising a vector comprising an AAV Cap expression cassette and an AAV Rep expression cassette but no hr after 9 passages. In various configurations, AAV production from an insect cell line comprising a vector comprising an AAV Cap expression cassette, an AAV Rep expression cassette and an hr of the present teachings can be, e.g., after 10 passages, at least 2-fold greater, at least 3-fold greater, or at least 4-fold greater than that of an insect cell line comprising a vector comprising an AAV Cap expression cassette and an AAV Rep expression cassette but no hr after 10 passages.

In some embodiments, the present teachings include methods of growing baculovirus in vitro. In these methods, baculovirus vectors comprising AAV Cap and AAV Rep cassettes can be used to infect or transfect (or co-infect or co-transfect) an insect cell in vitro such as, for example and without limitation, an Sf9 cell from *Spodoptera frugiperda*, or a cell in vitro from another insect such as, for example and without limitation, Tni Pro cells from *Trichoplusia ni* or E4a cells from *Estima acrea*. In various configurations, the cell can be co-infected with a transgene between inverted terminal repeats (ITRs) of AAV, such as, without limitation, ITRs of AAV5. In some configurations, a transgene can be a reporter gene, such as, for example and without limitation, a gene encoding a green fluorescent protein or a red fluorescent protein. An infected (or transfected) cell can be grown in vitro and thereby form a cell line that produces baculovirus. Such cell lines can be repeatedly passaged. In various configurations, the titer of baculovirus comprising an AAV gene such as a Cap gene or a Rep gene can be at least 20% of the titer of total baculovirus at passage P7 when the vector includes an hr. In various configurations, the titer of baculovirus comprising an AAV gene such as a Cap gene or a Rep gene can be at least 30% of the titer of total baculovirus at passage P7 when the vector includes an hr. In various configurations, the titer of baculovirus comprising an AAV gene such as a Cap gene or a Rep gene can be at least 40% of the titer of total baculovirus at passage P7 when the vector includes an hr. In various configurations, the titer of baculovirus comprising an AAV gene such as a Cap gene or a Rep gene can be at least 50% of the titer of total baculovirus at passage P7 when the vector includes an hr. In various configurations, the titer of baculovirus comprising an AAV gene such as a Cap gene or a Rep gene can be at least 60% of the titer of total baculovirus at passage P7 when the vector includes an hr. In various configurations, the titer of baculovirus comprising an AAV gene such as a Cap gene or a Rep gene can be at least 70% of the titer of total baculovirus at passage P7 when the vector includes an hr. In various configurations, the titer of baculovirus comprising an AAV gene such as a Cap gene or a Rep gene can be at least 80% of the titer of total baculovirus at passage P7 when the vector includes an hr. In various configurations, the titer of baculovirus comprising an AAV gene such as a Cap gene or a Rep gene can be at least 90% of the titer of total baculovirus at passage P7 when the vector includes an hr. In various configurations, the titer of baculovirus comprising an AAV gene such as a Cap gene or a Rep gene can be 100% of the titer of total baculovirus at passage P7 when the vector includes an hr. In various configurations, the titer of baculovirus comprising an AAV gene such as a Cap gene or a Rep gene can be at least 20% of the titer of total baculovirus at passage P10 when the vector includes an hr. In various configurations, the titer of baculovirus comprising an AAV gene such as a Cap gene or a Rep gene can be greater than 5% of the titer of total baculovirus at passage P10 when the vector includes an hr.

In some embodiments, the present teachings include methods of growing AAV in vitro. In these methods, insect cells comprising a vector of the present teachings including an hr can be grown and repeatedly passaged in vitro. In some configurations, relative yield of AAV at passage 7 (P7) from an insect cell line harboring a control vector without an hr can be less than 60% of AAV yield from an insect cell line harboring a vector that has an hr. In some configurations, relative yield of AAV at passage 7 (P7) from an insect cell line harboring a control vector without an hr can be less than 50% of AAV yield from an insect cell line harboring a vector that has an hr. In some configurations, relative yield of AAV at passage 7 (P7) from an insect cell line harboring a control vector without an hr can be less than 40% of AAV yield from an insect cell line harboring a vector that has an hr. In some configurations, relative yield of AAV at passage 7 (P7) from an insect cell line harboring a control vector without an hr can be less than 30% of AAV yield from an insect cell line harboring a vector that has an hr. In some configurations, relative yield of AAV at passage 7 (P7) from an insect cell line harboring a control vector without an hr can be less than 20% of AAV yield from an insect cell line harboring a vector that has an hr. In some configurations, relative yield of AAV at passage 10 (P10) from an insect cell line harboring a control vector without an hr can be less than 20% of AAV yield from an insect cell line harboring a vector that has an hr.

In some embodiments, a baculovirus vector of the present teachings can comprise an AAV Cap expression cassette, an AAV Rep expression cassette, and a baculovirus homologous region (hr) located up to about 4 kb from a start codon of an AAV expression cassette. In some configurations, the baculovirus vector can comprise, in 5' to 3' order, the Cap expression cassette, the Rep expression cassette, and the baculovirus homologous region (hr). In some configurations, the baculovirus vector can comprise, in 5' to 3' order, the Rep expression cassette, the Cap expression cassette, and the baculovirus homologous region (hr). In some configurations, a baculovirus vector can comprise, in 5' to 3' order, the Cap expression cassette, the baculovirus homologous region (hr), and the Rep expression cassette. In some configurations, the baculovirus vector can comprise, in 5' to 3' order, the Rep expression cassette, the baculovirus homologous region (hr), and the Cap expression cassette. In some configurations, the baculovirus vector can comprise, in 5' to 3' order, the baculovirus homologous region (hr), the Cap expression cassette, and the Rep expression cassette. In some configurations, the baculovirus vector can comprise, in 5' to 3' order, the baculovirus homologous region (hr), the Rep expression cassette, and the Cap expression cassette. In some configurations, the baculovirus vector can comprise an AAV Cap expression cassette; an AAV Rep expression cassette; and a baculovirus homologous region (hr) located up to about 4 kb from a start codon of an AAV expression cassette. In various configurations, a baculovirus vector of the present teachings can comprise an AAV Cap expression cassette, an AAV Rep expression cassette, and a baculovirus homologous region (hr) located up to about 4 kb from a start codon of an AAV expression cassette, wherein the hr region can be between the Rep expression cassette and the Cap expression cassette, and wherein the Rep expression cassette and the Cap expression cassette are in a head to head (5' to 5') orientation.

In various configurations, the baculovirus homologous region of a baculovirus vector of the present teachings can be an hr2 sequence.

In various configurations, a baculovirus vector of the present teachings can comprise an AAV Cap expression cassette, an AAV Rep expression cassette, and a baculovirus homologous region (hr) located up to about 4 kb from a start codon of an AAV expression cassette, wherein the vector can be exclusive of a Rep binding element (RBE).

In various configurations, the present teachings include an insect cell line comprising cells comprising a baculovirus vector, wherein the vector can comprise an AAV Cap expression cassette, an AAV Rep expression cassette, and a baculovirus homologous region (hr) located up to about 4 kb from a start codon of an AAV expression cassette. In some configurations, the vector can comprise in 5' to 3' order, the Cap expression cassette, the Rep expression cassette, and the baculovirus homologous region (hr). In various configurations, the vector can comprise, in 5' to 3' order, the Rep expression cassette, the Cap expression cassette, and the baculovirus homologous region (hr). In various configurations, the vector can comprise, in 5' to 3' order, the Cap expression cassette, the baculovirus homologous region (hr), and the Rep expression cassette. In various configurations, the vector can comprise, in 5' to 3' order, the Rep expression cassette, the baculovirus homologous region (hr), and the Cap expression cassette. In various configurations, the vector can comprise, in 5' to 3' order, the baculovirus homologous region (hr), the Cap expression cassette, and the Rep expression cassette. In various configurations, the vector can comprise, in 5' to 3' order, the baculovirus homologous region (hr), the Rep expression cassette, and the Cap expression cassette. In various configurations, the hr region can be between the Rep expression cassette and the Cap expression cassette, and the Rep expression cassette and the Cap expression cassette can be in a head to head (5' to 5') orientation. In various configurations, the baculovirus homologous region can be an hr2 sequence. In various configurations, the vector can be exclusive of a Rep binding element (RBE).

In various embodiments, the present teachings include methods of growing baculovirus in vitro. In various aspects, a method of the present teachings can comprise providing a culture of insect cells comprising a baculovirus vector, wherein the vector can comprise an AAV Cap expression cassette, an AAV Rep expression cassette, and a baculovirus homologous region (hr) located up to about 4 kb from a start codon of an AAV expression cassette, and incubating the cells. In some configurations, a culture of insect cells of the present teachings can further comprise a second vector. In various configurations, the second vector can comprise a transgene flanked by AAV ITRs. In various configurations, incubating the cells can comprise passaging the cells. In some configurations, AAV production yield at passage 7 can be at least 2-fold greater compared to a control insect cell line comprising a baculovirus vector comprising an AAV Cap expression cassette and an AAV Rep expression cassette but no baculovirus hr. In some configurations, the titer of baculovirus comprising the AAV Cap expression cassette at passage 7 can be greater than 21.5% of total baculovirus titer (as measured by qPCR of gp64 for total BV and of Cap for AAV).

In various embodiments, the present teachings include methods of growing AAV in vitro. In various configurations, these methods can comprise providing a culture of insect cells, infecting or transfecting the insect cells with a baculovirus vector in accordance with the present teachings, and incubating the cells. In some configurations the vector comprised by the cells can comprise an AAV Cap expression cassette, an AAV Rep expression cassette, and a baculovirus homologous region (hr) located up to about 4 kb from a start codon of an AAV expression cassette. In some configurations, the vector comprised by the cells can comprise in 5' to 3' order, the Cap expression cassette, the Rep expression cassette, and the baculovirus homologous region (hr). In various configurations, the vector comprised by the cells can comprise, in 5' to 3' order, the Rep expression cassette, the Cap expression cassette, and the baculovirus homologous region (hr). In various configurations, the vector comprised by the cells can comprise, in 5' to 3' order, the Cap expression cassette, the baculovirus homologous region (hr), and the Rep expression cassette. In various configurations, the vector comprised by the cells can comprise, in 5' to 3' order, the Rep expression cassette, the baculovirus homologous region (hr), and the Cap expression cassette. In various configurations, the vector comprised by the cells can comprise, in 5' to 3' order, the baculovirus homologous region (hr), the Cap expression cassette, and the Rep expression cassette. In various configurations, the vector comprised by the cells can comprise, in 5' to 3' order, the baculovirus homologous region (hr), the Rep expression cassette, and the Cap expression cassette. In various configurations, the hr region comprised by the vector can be between the Rep expression cassette and the Cap expression cassette, and the Rep expression cassette and the Cap expression cassette can be in a head to head (5' to 5') orientation. In various configurations, the baculovirus homologous region comprised by the vector comprised by the cells can be an hr2 sequence. In various configurations, the vector comprised by the cells can be exclusive of a Rep binding element (RBE). In various configurations, the yield at P7 of AAV from the insect cells can be at least 50°.% greater than the yield at P7 of AAV from insect cells comprising a baculovirus vector without the hr. In various configurations, the yield at P7 of AAV from cells comprising the baculovirus hr can be at least 20% greater than the yield of AAV from cells comprising a baculovirus vector without the hr. In various configurations, the baculovirus vector can be exclusive of a Rep binding element (RBE).

In various embodiments, a method of producing AAV in vitro can comprise growing an insect cell culture comprising a vector of the present teachings, and a vector comprising a transgene flanked by AAV ITRs. In some configurations the vector comprised by the cells can comprise an AAV Cap expression cassette, an AAV Rep expression cassette, and a baculovirus homologous region (hr) located up to about 4 kb from a start codon of an AAV expression cassette. In some configurations, the vector comprised by the cells can comprise in 5' to 3' order, the Cap expression cassette, the Rep expression cassette, and the baculovirus homologous region (hr). In various configurations, the vector comprised by the cells can comprise, in 5' to 3' order, the Rep expression cassette, the Cap expression cassette, and the baculovirus homologous region (hr). In various configurations, the vector comprised by the cells can comprise, in 5' to 3' order, the Cap expression cassette, the baculovirus homologous region (hr), and the Rep expression cassette. In various configurations, the vector comprised by the cells can comprise, in 5' to 3' order, the Rep expression cassette, the baculovirus homologous region (hr), and the Cap expression cassette. In various configurations, the vector comprised by the cells can comprise, in 5' to 3' order, the baculovirus homologous region (hr), the Cap expression cassette, and the Rep expression cassette. In various configurations, the vector comprised by the cells can comprise, in 5' to 3' order, the baculovirus homologous region (hr), the Rep expression cassette, and the Cap expression cassette. In various configurations, the hr region comprised by the vector can be between the Rep expression cassette and the Cap expression cassette, and the Rep expression cassette and the Cap expression cassette can be in a head to head (5' to 5') orientation. In various configurations, the baculovirus homologous region comprised by the vector comprised by the cells can be an hr2 sequence. In various configurations, the vector comprised by the cells can be exclusive of a Rep binding element (RBE).

In various embodiments, the present teachings can include a baculovirus vector without a Rep binding element (RBE) for producing AAV in insect cells in vitro, which can comprise an AAV Cap expression cassette, an AAV Rep expression cassette, and a baculovirus homologous region (hr) located up to about 4 kb of a start codon of an AAV expression cassette.

BRIEF DESCRIPTION OF THE DRAWINGS

FIG. 9A-H illustrates comparative recombinant baculovirus (rBV) titers with or without the hr2 sequence from passage 3 to passage 10.

FIG. 10A-E illustrates comparative AAV production yields between recombinant baculoviruses (rBVs) with or without the hr2 sequence from passage 3 to passage 10 or at passage 10 between AAV strains.

DETAILED DESCRIPTION

Methods and compositions described herein utilize laboratory techniques well known to skilled artisans, and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; Nagy, A., Manipulating the Mouse Embryo: A Laboratory Manual (Third Edition), Cold Spring Harbor, N.Y., 2003 and Harlow, E., Using Antibodies: A Laboratory Manual, Cold Spring Harbor Laboratory Press, Cold Spring Harbor, N.Y., 1999. As used in the present description and any appended claims, the singular forms "a", "an" and "the" are intended to include the plural forms as well, unless the context indicates otherwise.

The following materials and methods are also used in various aspects of the present teachings.

Insect Cell Culture

Spodoptera frugiperda Sf9 cells, Trichoplusia ni cells, and Estima acrea cells were cultured in coming storage bottles at 28° C. in ESF921 medium (Expression Systems, Davis, Calif.) supplemented with 100 units/ml penicillin and 100 µg/ml streptomycin. The cells were split 1:4 once the cell density reaches $8 \times 10^6$ cells/mi for maintenance.

Plasmid Construction and Recombinant Baculovirus Generation

The hr2 sequence was PCR amplified from the baculovirus genome and cloned into plasmid V053-pFBD-inRepOpt-inCap8 to create V059-pFBD-inRepOpt-hr2-inCap8. In order to include the kozak sequence, plasmid V059 was cut with BstZ17I and AgeI to remove the BstZ17I-AgeI fragment and replaced with the BstZ17I-AgeI fragment with kozak sequence upstream of VP1 start codon from V150-pFB-inCap8-inRep-kozak to create V277-pFB-inCap8-hr2-inRep-kozak where the hr2 is located between the Rep and the Cap expression cassettes. To insert the hr2 sequence into another location after the polyA sequence of the Rep expression cassette, the hr2 sequence was PCR amplified with primers 3205F (5'-GCTTTACGAGTAGAATTC-TACGTGT-3' SEQ ID NO: 7) and 3206R (5'-GGCC-TACGTAGTTTACACGTAGAATTCTACTCGT-3' SEQ ID NO: 8) from V277. The pc promoter sequence was amplified with primers 3065F (5'-ATTTGACTTGGTCAGGGCCG-3' SEQ ID NO: 9) and 3204R (5'-GAATTC-TACTCGTAAAGCCCAGTTGACATAAGCCTGTTCG-3' SEQ ID NO: 10) from V150. These hr2 and pc promoter PCR fragments were joined together through a second PCR reaction with primers 3065F and 3206R. The joined PCR fragment was digested with BsrG1 and SnaBI and ligated into the BsrG1 and SnaBI sites of V150, V212, V195, V188, and V146 to create V288-pFB-inCap8-inRep-hr2, V289-pFB-inCap9-inRep-hr2, V290-pFB-inCap6-inRep-hr2, V291-pFB-inCap1-inRep-hr2, and V295-pFB-inCap5-in- Rep-hr2 respectively. Examples of plasmids with an hr sequence insertion are illustrated in FIGS. 1-6.

Figure 1:
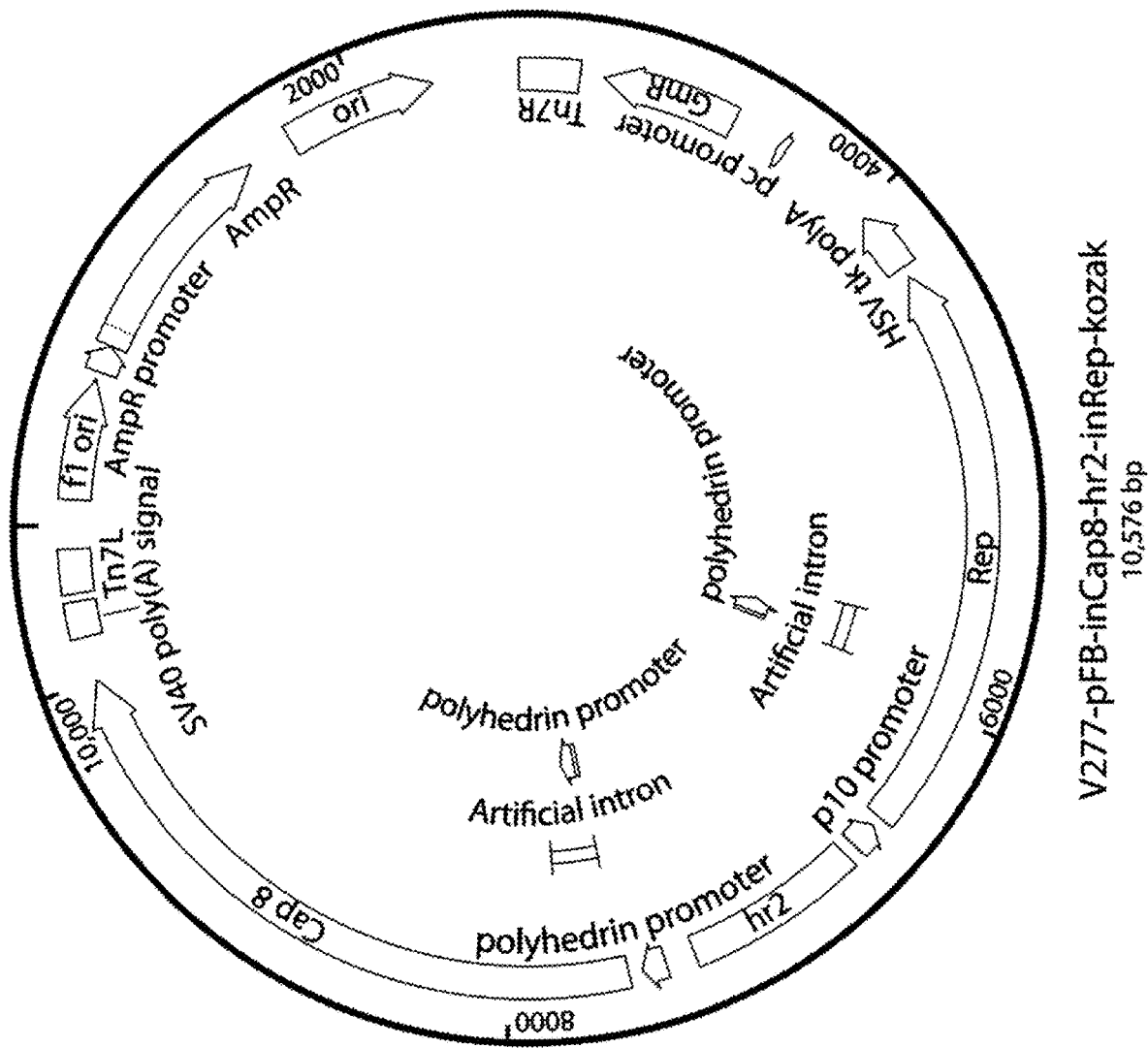
FIG. 1 illustrates a baculovirus shuttle plasmid of the present teachings, comprising an hr2 sequence between an AAV8 capsid gene and an AAV2 rep gene.
Figure 2:
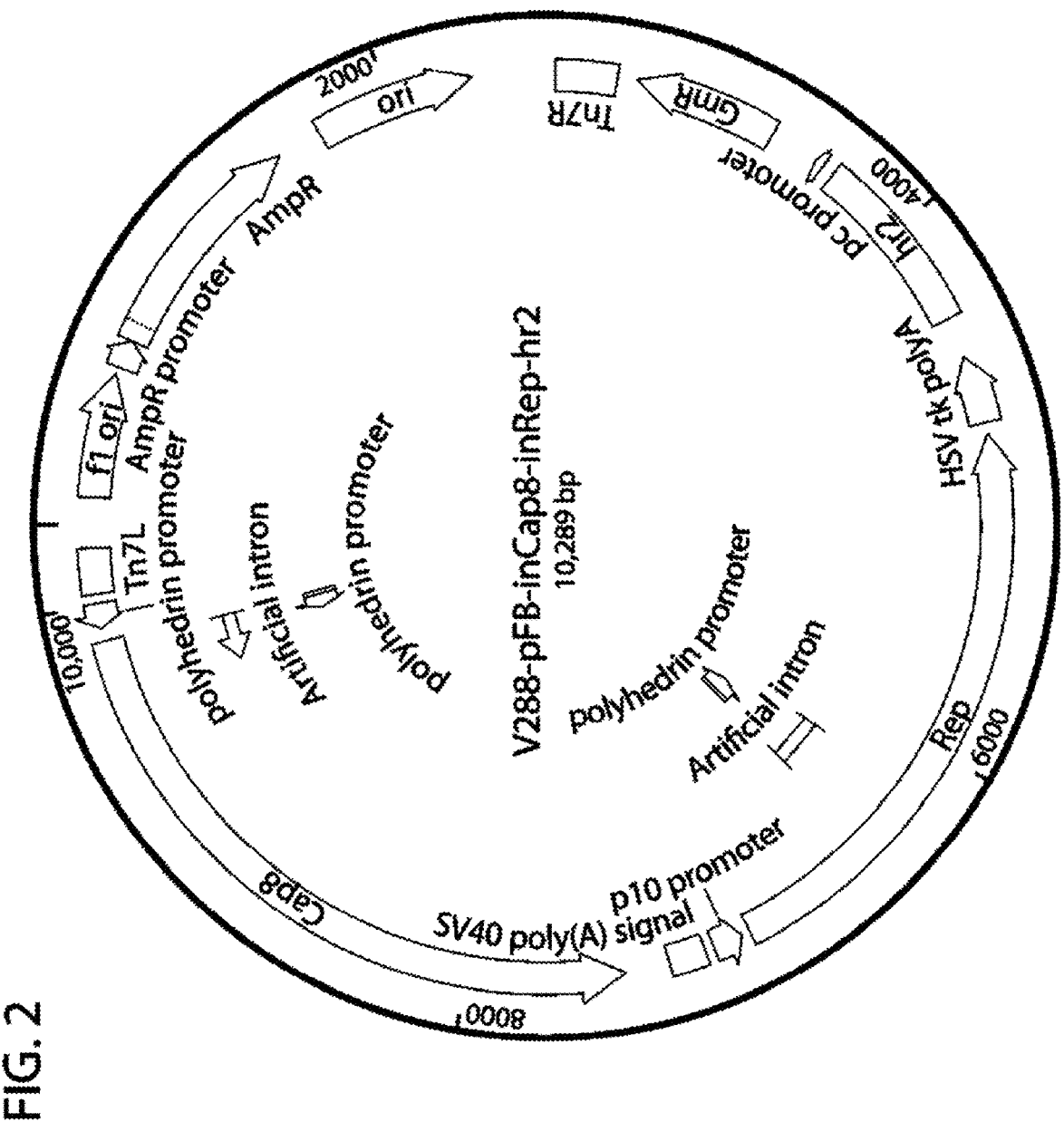
FIG. 2 illustrates a baculovirus shuttle plasmid of the present teachings, comprising an AAV8 Cap gene, and an hr2 sequence between an AAV2 rep gene and a gentamicin resistance (GmR) gene.
Figure 3:
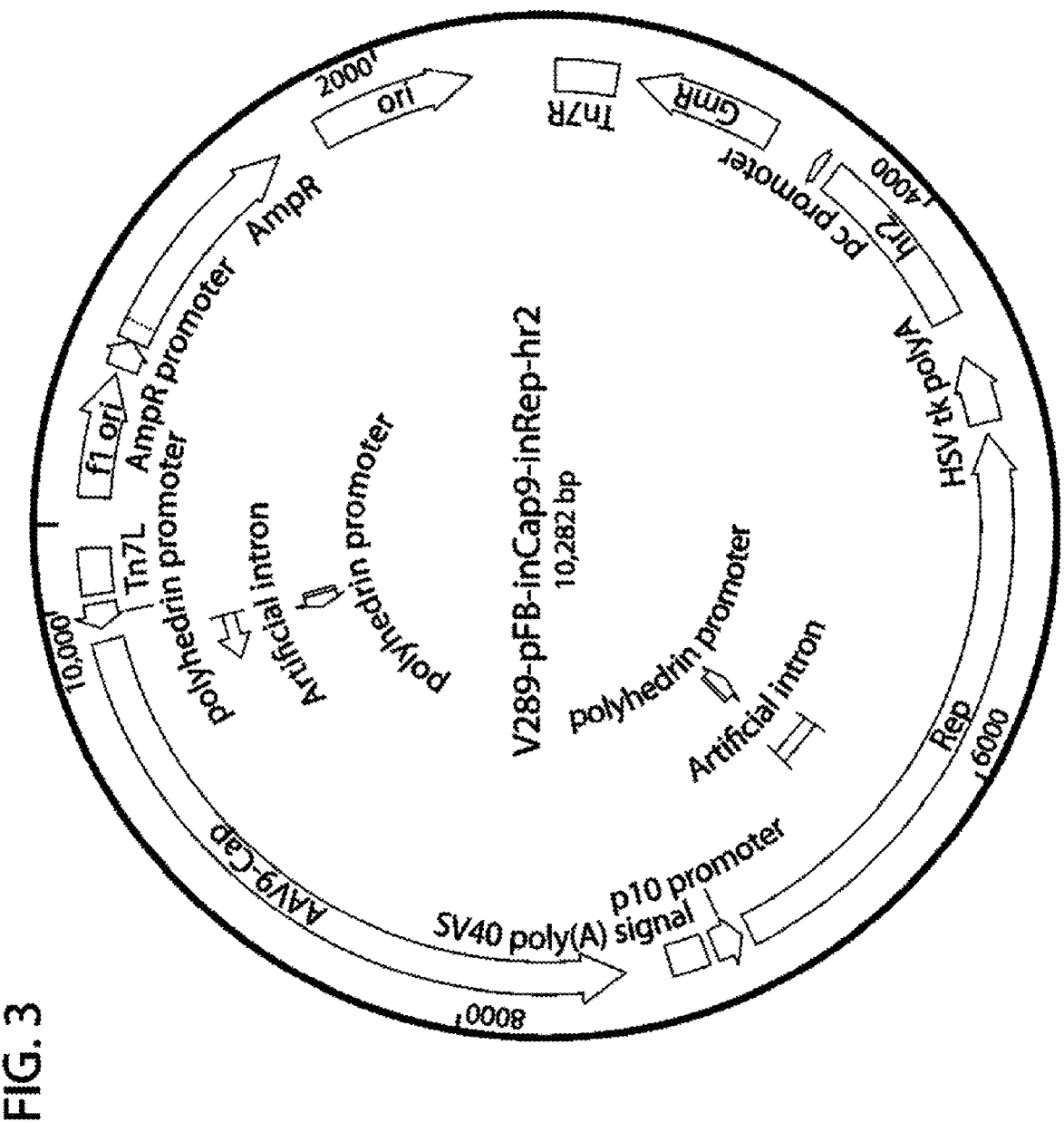
FIG. 3 illustrates a baculovirus shuttle plasmid of the present teachings, comprising an AAV9 Cap gene, and an hr2 sequence between an AAV2 rep gene and a gentamicin resistance (GmR) gene.
Figure 4:
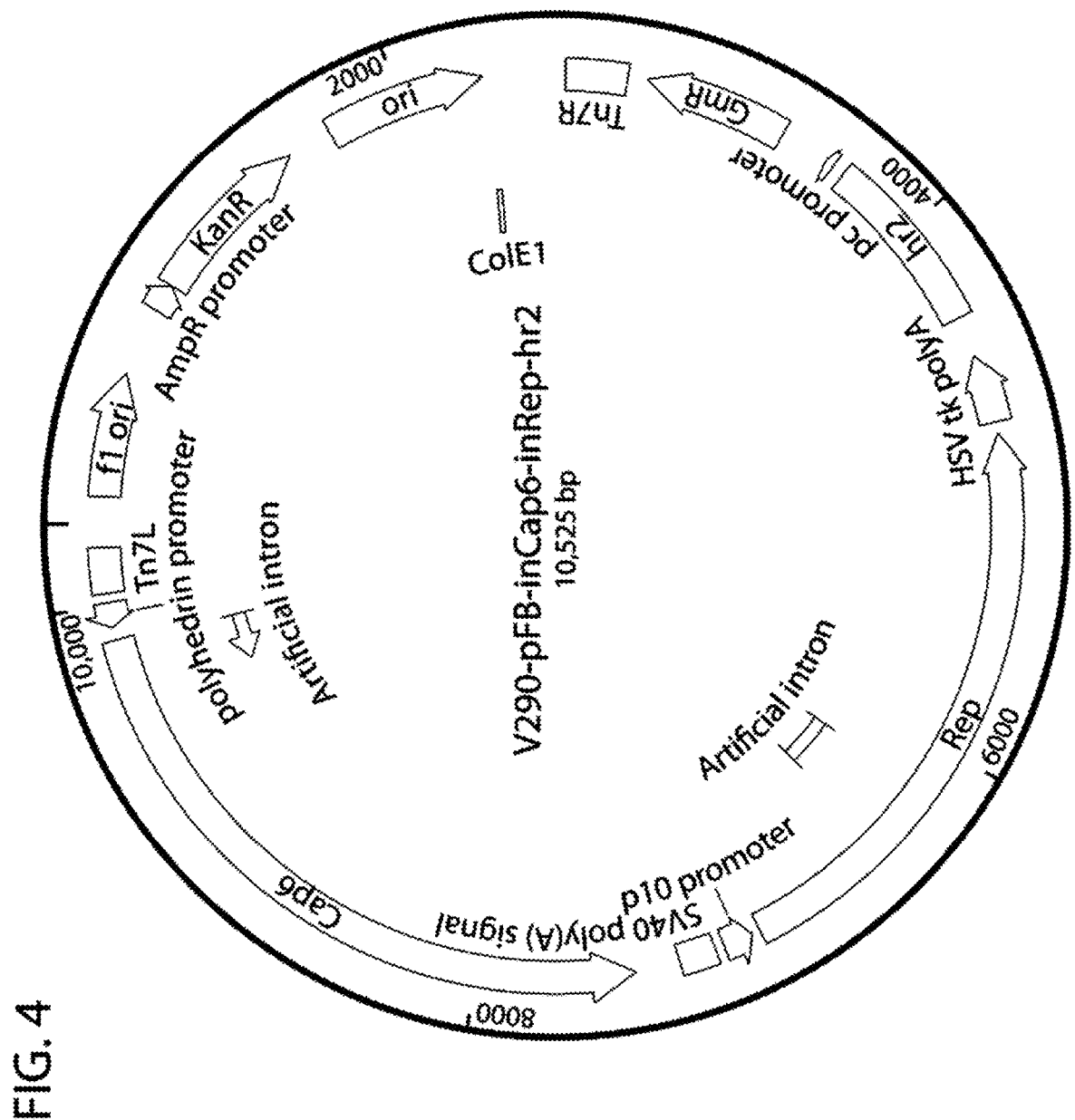
FIG. 4 illustrates a baculovirus shuttle plasmid of the present teachings, comprising an AAV6 Cap gene, and an hr2 sequence between an AAV2 rep gene and a gentamicin resistance (GmR) gene.
Figure 5:
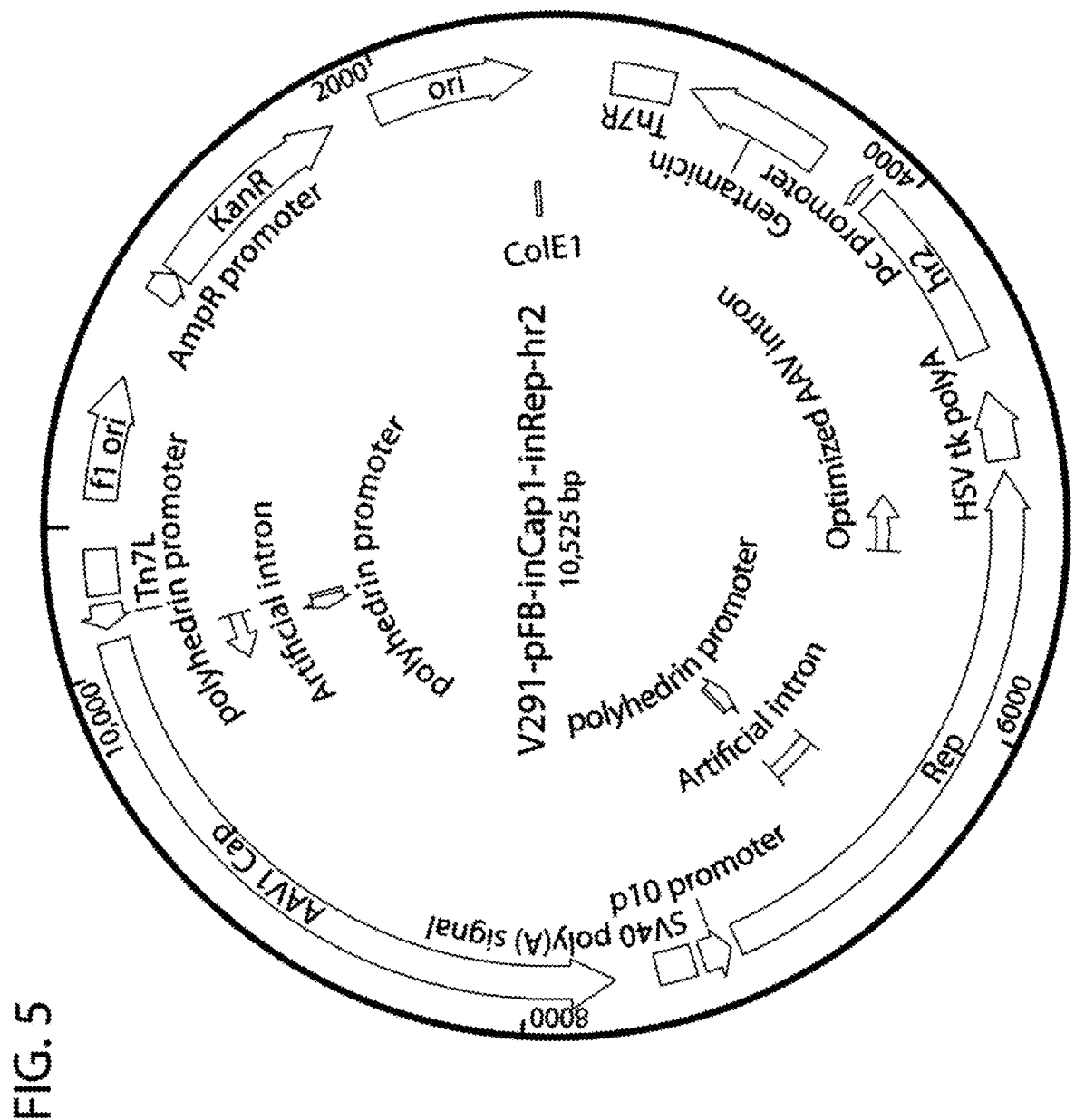
FIG. 5 illustrates a baculovirus shuttle plasmid of the present teachings, comprising an AAV1 Cap gene, and an hr2 sequence between an AAV2 rep gene and a gentamicin resistance (GmR) gene.
Figure 6:
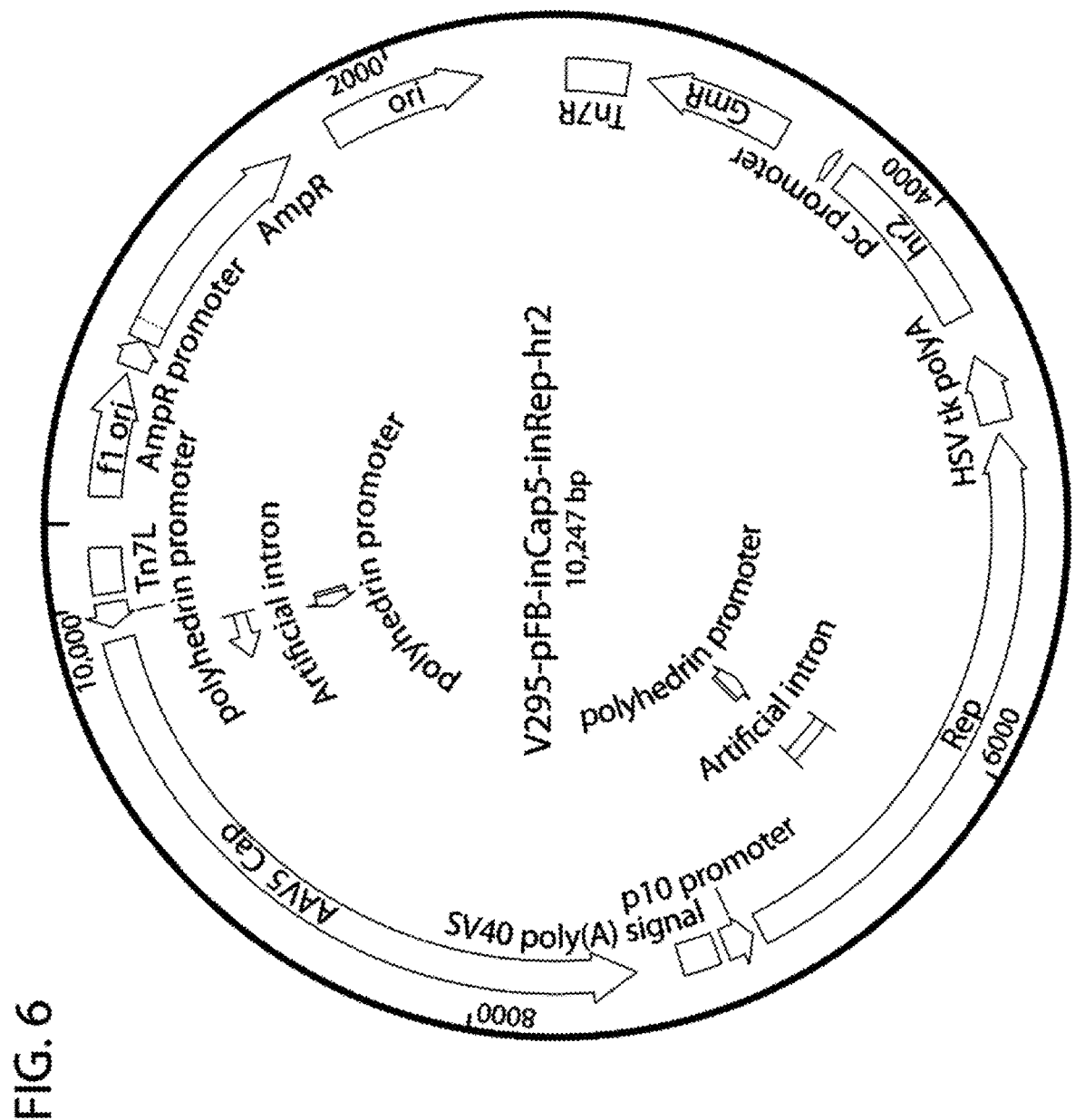
FIG. 6 illustrates a baculovirus shuttle plasmid of the present teachings, comprising an AAV5 Cap gene, and an hr2 sequence between an AAV2 rep gene and a gentamicin resistance (GmR) gene.
Figure 7:
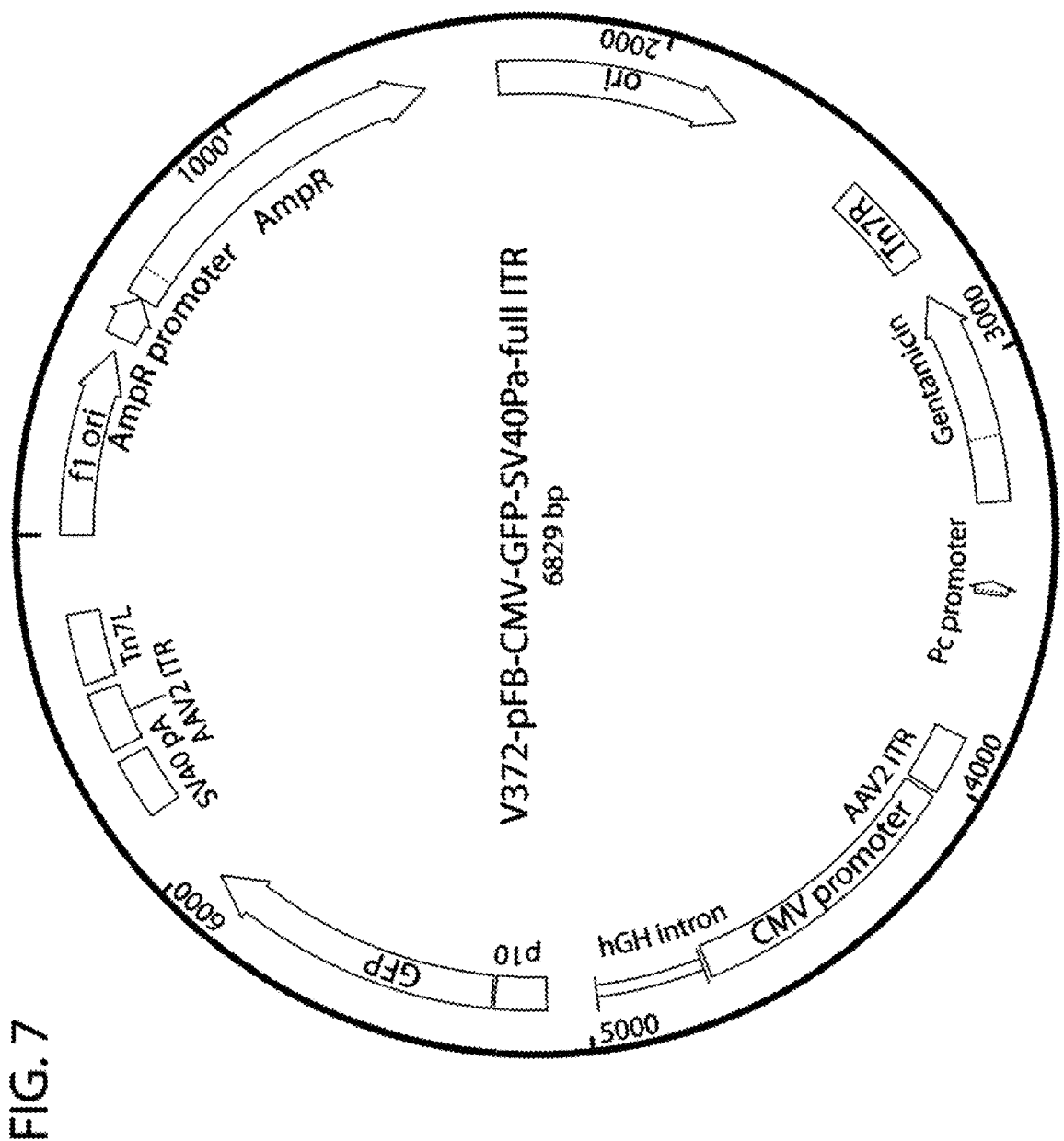
FIG. 7 illustrates the GFP expression cassette flanked by two ITRs in baculovirus shuttle plasmid V372-pFB-CMV-GFP-SV40 pA-full ITR.

Plasmid pFB-CMV-GFP was constructed by PCR amplifying the GFP fragment which was then cloned into the multiple cloning sites of V032-pFB-CMV-SV40 pA (FIG. 7)

The plasmids were used to generate bacmids according to manufacturer's protocol (Invitrogen). Briefly, plasmids were diluted to a concentration of 2 ng/µl and 2 µl of plasmid DNA was used to transform DH10Bac competent cells. After 2 days of incubation, white colonies were picked and miniprep bacmid DNAs were prepared. The miniprep bacmid DNAs were used to transfect S9 cells to generate recombinant baculoviruses.

Plaque Purification and Passaging of Recombinant Baculovirus

The generated recombinant baculoviruses were plaque purified in order to get homogenous clones. Briefly, Sf9 cells were plated on 6-well plates with cell density of 1.5e+6 cells % well in 2 ml ESF921 media and incubated at 28° C. for 30 min. The baculoviruses were each diluted to $10^{-2}$, $10^{-3}$, $10^{-4}$, $10^{-5}$, $10^{-6}$, and $10^{-7}$ in 1 ml volume. At the end of incubation, media were removed from the wells and 250 µl of each dilution was added to infect the Sf9 cells at 28° C. for 1 hour. At the end of the incubation, 3 ml of 1% agarose overlay (cool down to 42° C.) was added to the wells. When the agarose was solidified, 2 ml of ESF921 media was added to each well and the plates were incubated at 28° C. for 5 to 7 days. Well-formed plaques were picked and used to infect insect cells for passaging.

To passage the plaque purified recombinant baculoviruses, insect cells were infected with about 1 moi of the viruses for 3 days at 28° C. and supernatant was harvested. The harvested viruses were used to infect fresh insect cells again and so on until passage 10.

Real-Time Quantitative PCR (qPCR) Quantification of Recombinant Baculoviruses and AAV Vectors To determine the titers of recombinant baculoviruses and AAV, a qPCR method was employed. It was empirically determined that one plaque-forming unit (pfu) comprises about 20 genome copies of the virus. Briefly, harvested viruses were diluted in qPCR dilution buffer and heated to 95° C. for 30 min to break the virus particles. The treated virus samples were then assayed in the CHROMO4™ system (Bio-Rad Laboratories, Inc., Hercules, Calif.) together with a known standard. The Ct values were converted to pfu and used to guide the baculovirus passaging and AAV production.

AAV Vector Production and Quantification

Recombinant baculoviruses were used to infect insect cells to produce AAV vectors. Briefly, 10 moi of recombinant baculovirus containing the Rep and Cap genes with or without the hr2 sequence were co-infected with 5 moi of recombinant baculovirus containing the GFP marker gene flanked by AAV ITRs for 3 days at 28° C. Cell pellets were collected by centrifugation at 3000 rpm for 10 min. The cell pellets were lysed in SF9 lysis buffer (50 mM Tris-HCl, pH7.8, 50 mM NaCl, 2 mM $MgCl_2$, 1% Sarkosyl, 1% Triton X-100, and 140 units/ml Benzonase) by sonication. Cell debris was removed by centrifugation at 8000 rpm for 20 min. The cleared lysates were used for quantification of AAV productivity as follows: the lysates were diluted with qPCR dilution buffer and contaminating DNA was destroyed by incubating with DNase I enzyme at 37° C. for 1 hour. The DNase I enzyme was inactivated by heating at 95° C. for 30 min. in the presence of 100 mM EDTA. The treated AAV samples were further diluted and assayed in the Chromo4 qPCR machine. The Ct values were converted to AAV vector genome copies.

Western Blot Analysis

Recombinant baculoviruses containing the rep and cap genes were used to infect Sf9 cells for three days and cell pellets were harvested by centrifugation at 3,000 rpm for 10 min. The cell pellets with about $2 \times 10^6$ cells were first resuspended in 300 µl of PBS buffer and then vortexed with 100 µl of 4×LDS sample buffer to lyse the cells. The lysates were heated at 95° C. for 5 min and then sonicated for 20 seconds to shear the genomic DNA. After brief centrifugation, the lysates were then loaded onto a 10% SDS-gel to separate the proteins. The proteins were then transferred from the gel to nitrocellulose membranes. After blocking with 5% skim milk, the membranes were probed with specific antibodies against the rep or cap proteins. A second antibody coupled with horseradish peroxidase (HRP) against the first antibody was used to detect the rep or cap proteins through color matrix reaction.

EXAMPLES

The present teachings including descriptions provided in the Examples that are not intended to limit the scope of any claim or aspect. Unless specifically presented in the past tense, an example can be a prophetic or an actual example. The following non-limiting examples are provided to further illustrate the present teachings. Those of skill in the art, in light of the present disclosure, will appreciate that many changes can be made in the specific embodiments that are disclosed and still obtain a like or similar result without departing from the spirit and scope of the present teachings.

Example 1

This example illustrates a shuttle vector of the present teachings.

In this plasmid (FIG. 1), an hr2 sequence is located between an AAV8 capsid gene cassette and an AAV2 rep gene cassette. The vector includes the Cap and Rep genes in head-to-head orientation. This shuttle plasmid was used to generate recombinant baculovirus (rBV), which in turn was used to produce AAV8 in insect cells.

Example 2

This example illustrates a shuttle vector of the present teachings.

In this plasmid (FIG. 2), an hr2 sequence is located between an AAV2 rep gene cassette and a gentamicin resistance (GmR). The vector also includes an AAV8 capsid gene cassette. The Cap and Rep genes are in a head-to-tail orientation. This plasmid was used to generate recombinant baculovirus (rBV), which in turn was used to produce AAV8 in insect cells.

Example 3

This example illustrates a shuttle vector of the present teachings.

In this plasmid (FIG. 3), an hr2 sequence is located between an AAV2 rep gene cassette and a gentamicin resistance (GmR). The vector also includes an AAV9 capsid gene cassette. The Cap and Rep genes are in a head-to-tail orientation. This plasmid was used to generate recombinant baculovirus (rBV), which in turn was used to produce AAV9 in insect cells.

Example 4

This example illustrates a shuttle vector of the present teachings.

In this plasmid (FIG. 4), an hr2 sequence is located between an AAV2 rep gene cassette and a gentamicin resistance (GmR). The vector also includes an AAV6 capsid gene cassette. The Cap and Rep genes are in a head-to-tail orientation. This plasmid was used to generate recombinant baculovirus (rBV), which in turn was used to produce AAV6 in insect cells.

Example 5

This example illustrates a shuttle vector of the present teachings.

In this plasmid (FIG. 5), an hr2 sequence is located between an AAV2 rep gene cassette and a gentamicin resistance (GmR). The vector also includes an AAV1 capsid gene cassette. The Cap and Rep genes are in a head-to-tail orientation. This plasmid was used to generate recombinant baculovirus (rBV), which in turn was used to produce AAV1 in insect cells.

Example 6

This example illustrates a shuttle vector of the present teachings.

In this plasmid (FIG. 6), an hr2 sequence is located between an AAV2 rep gene cassette and a gentamicin resistance (GmR). The vector also includes an AAV5 capsid gene cassette. The Cap and Rep genes are in a head-to-tail orientation. This plasmid was used to generate recombinant baculovirus (rBV), which in turn was used to produce AAV5 in insect cells.

Example 7

This example illustrates that an hr sequence enhances yields of AAV production.

Figure 8:
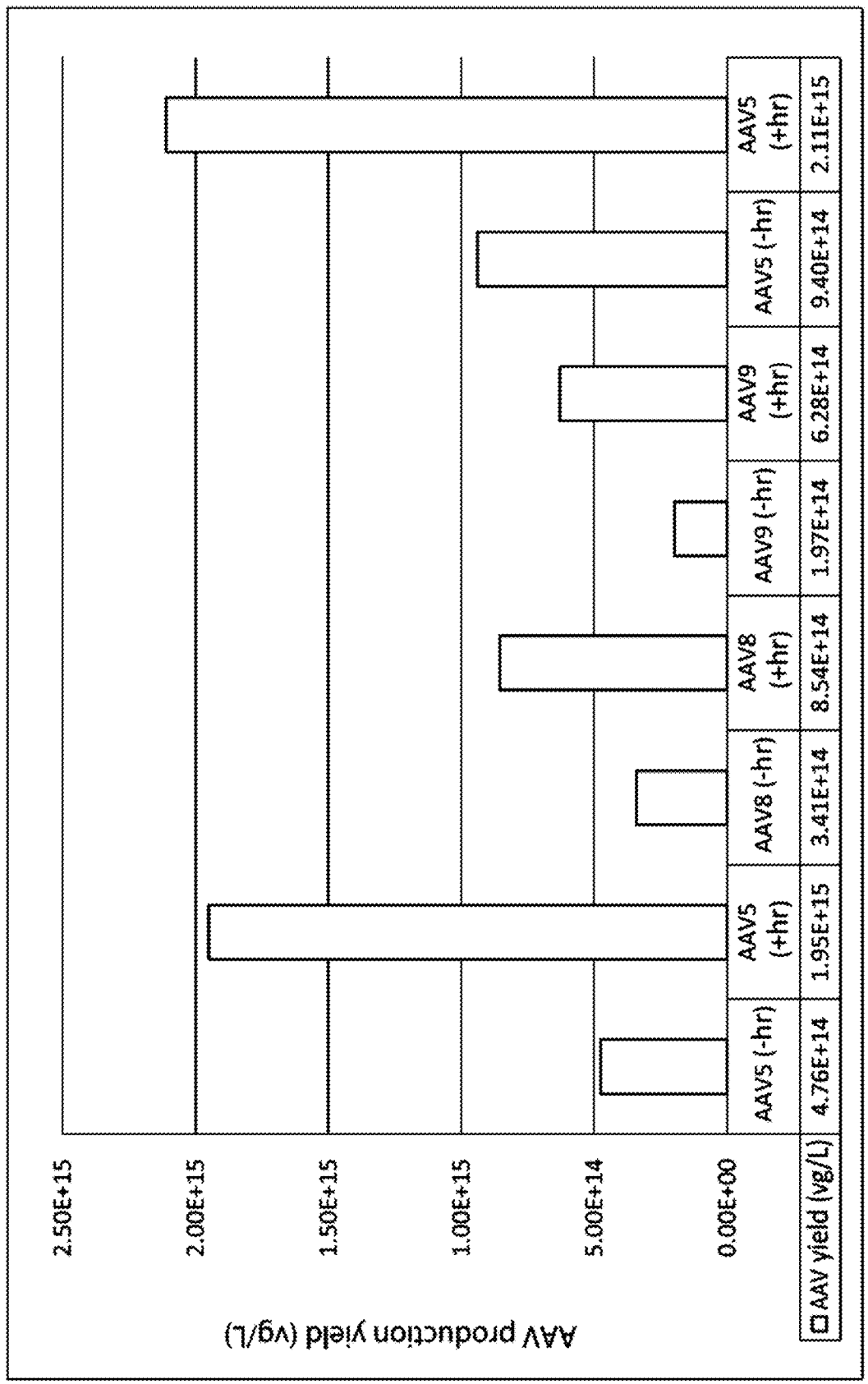
FIG. 8 illustrates comparative AAV production yields by recombinant baculoviruses (rBVs) with or without the hr2 sequence.

In these experiments, the hr2 sequence was cloned either between the Rep and the Cap expression cassettes in plasmid V277 (FIG. 1) or after the poly A sequence of the Rep expression cassette in plasmids V289 (FIG. 3) and V295 (FIG. 6) and recombinant baculoviruses were prepared. These recombinant baculoviruses were used to coinfect Sf9 cells with recombinant baculovirus carrying GFP gene for AAV production. The results are shown in FIG. 8. The data indicate that hr2 sequence enhances the AAV productivity irrespective of the location of the hr2 sequence and AAV serotypes. The increase of AAV productivity ranged from 2- to 4-fold compared to controls lacking an hr.

Example 8

This example illustrates that an hr sequence enhances stability of recombinant baculoviruses containing the AAV rep and cap genes.

In these experiments, to further analyze the stability of recombinant baculoviruses with or without the hr2 sequence, plaque purification and passaging of the recombinant baculoviruses multiple times were employed. A pair of qPCR primers—gp64F (5'-CCCTCTGTGTACTTGG-CTCTAACG-3' SEQ ID NO: 11) and gp64R (5'-CGGT-GAAACGCAAAGTCGAGCACCG-3' SEQ ID NO: 12)—corresponding to the gp64 gene (present in all recombinant baculoviruses of the present teachings) was used to determine total baculovirus titer. For baculoviruses comprising the Rep and Cap expression cassettes, a pair of qPCR primers—Rep2F (5'-ATTCATOCTCCACCTCAACC-3' SEQ ID NO: 13) and Rep2R (5'-GCCGTCTGGAT-CATGACTIT-3' SEQ ID NO: 14)-corresponding to the Rep sequence was used to determine titer of these baculoviruses.

Figure 9A:
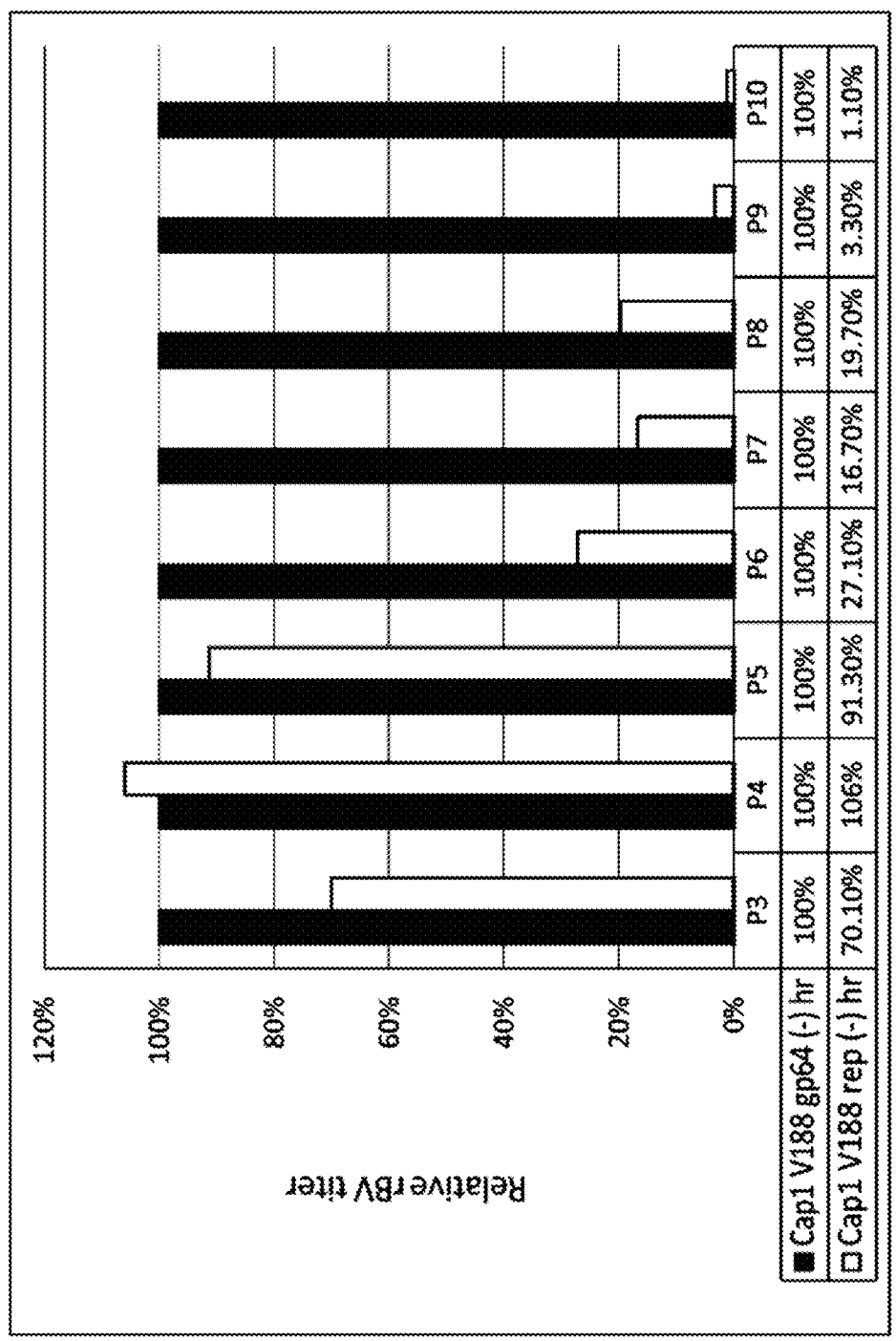
Figure 9B:
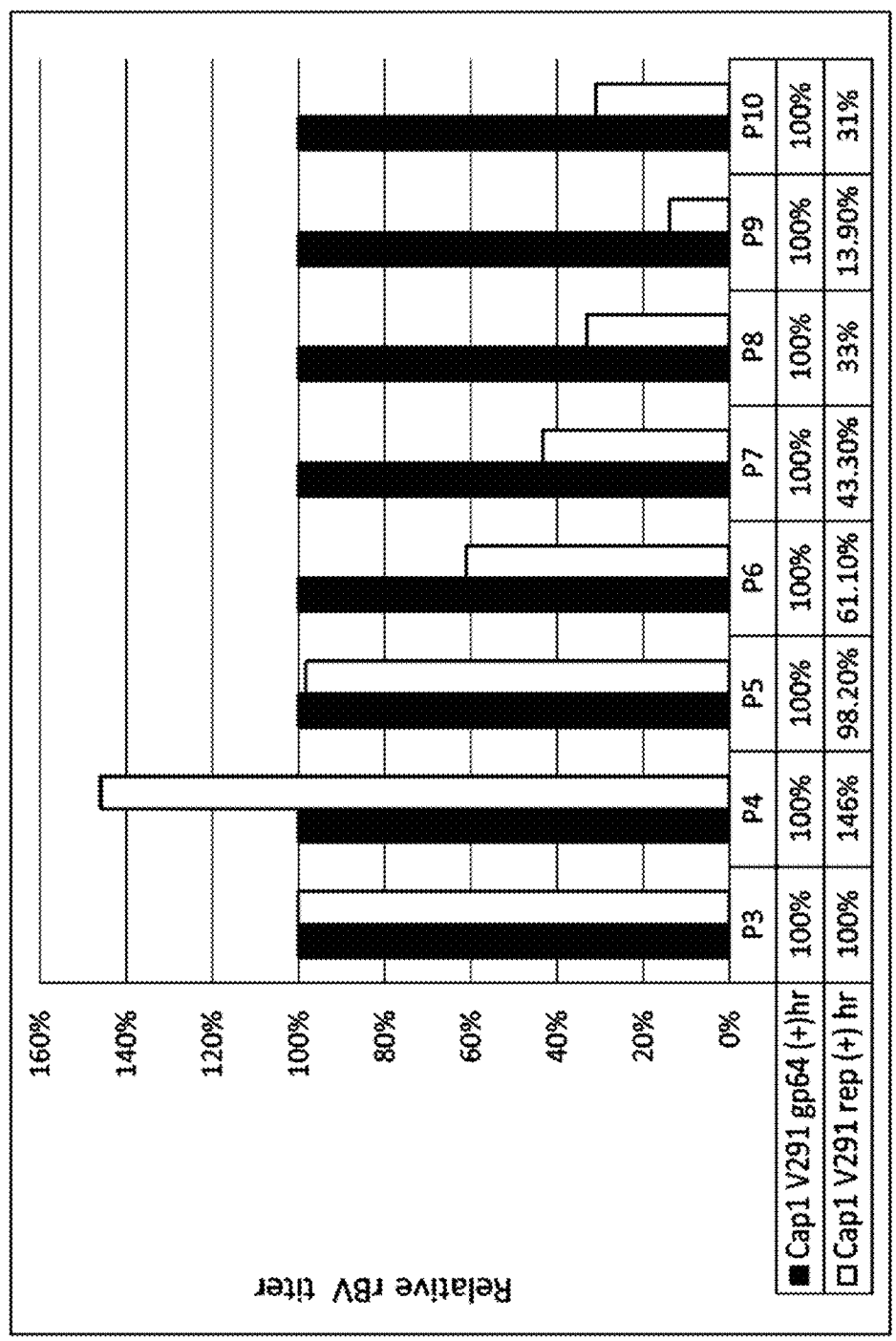
Figure 9D:
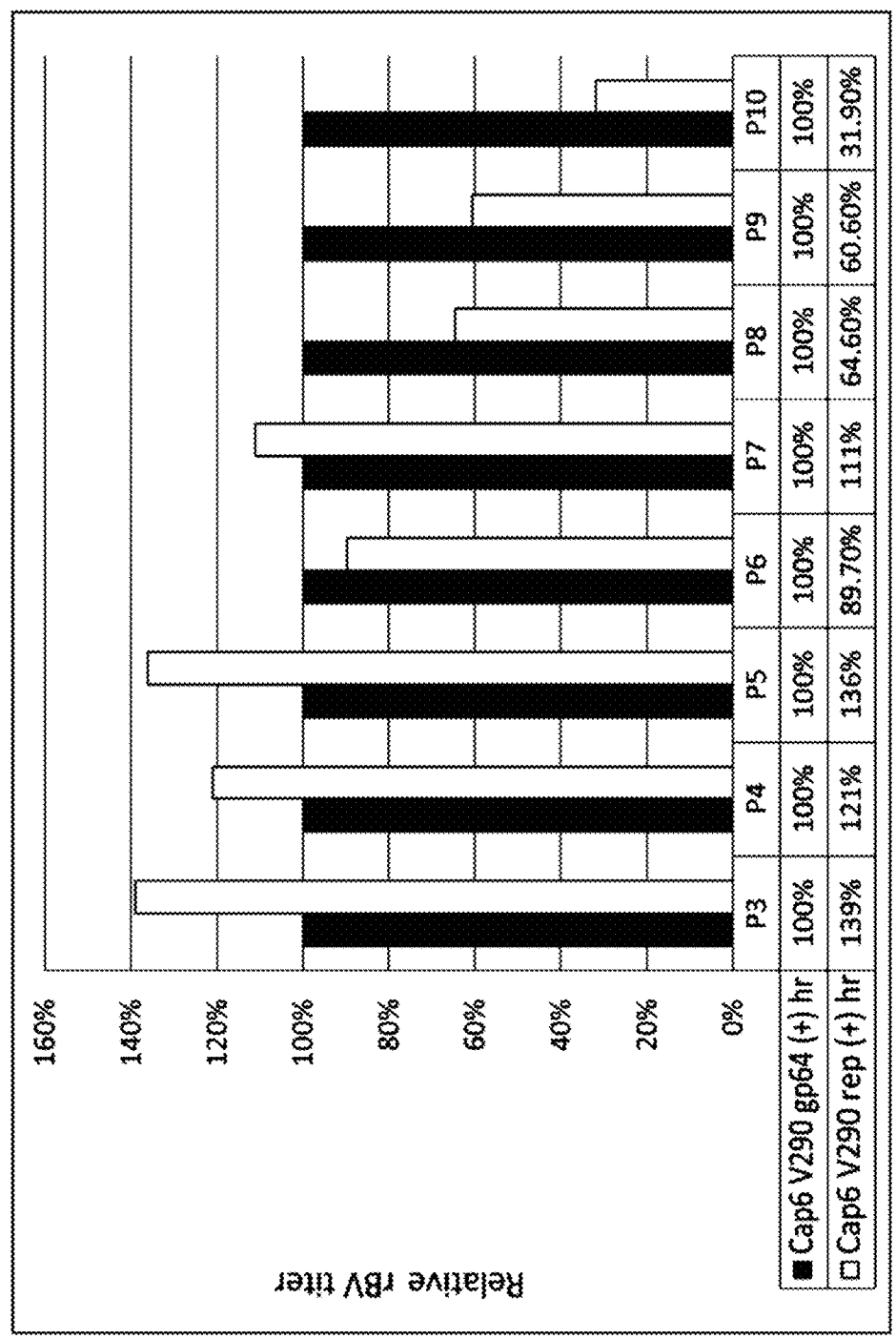
Figure 9E:
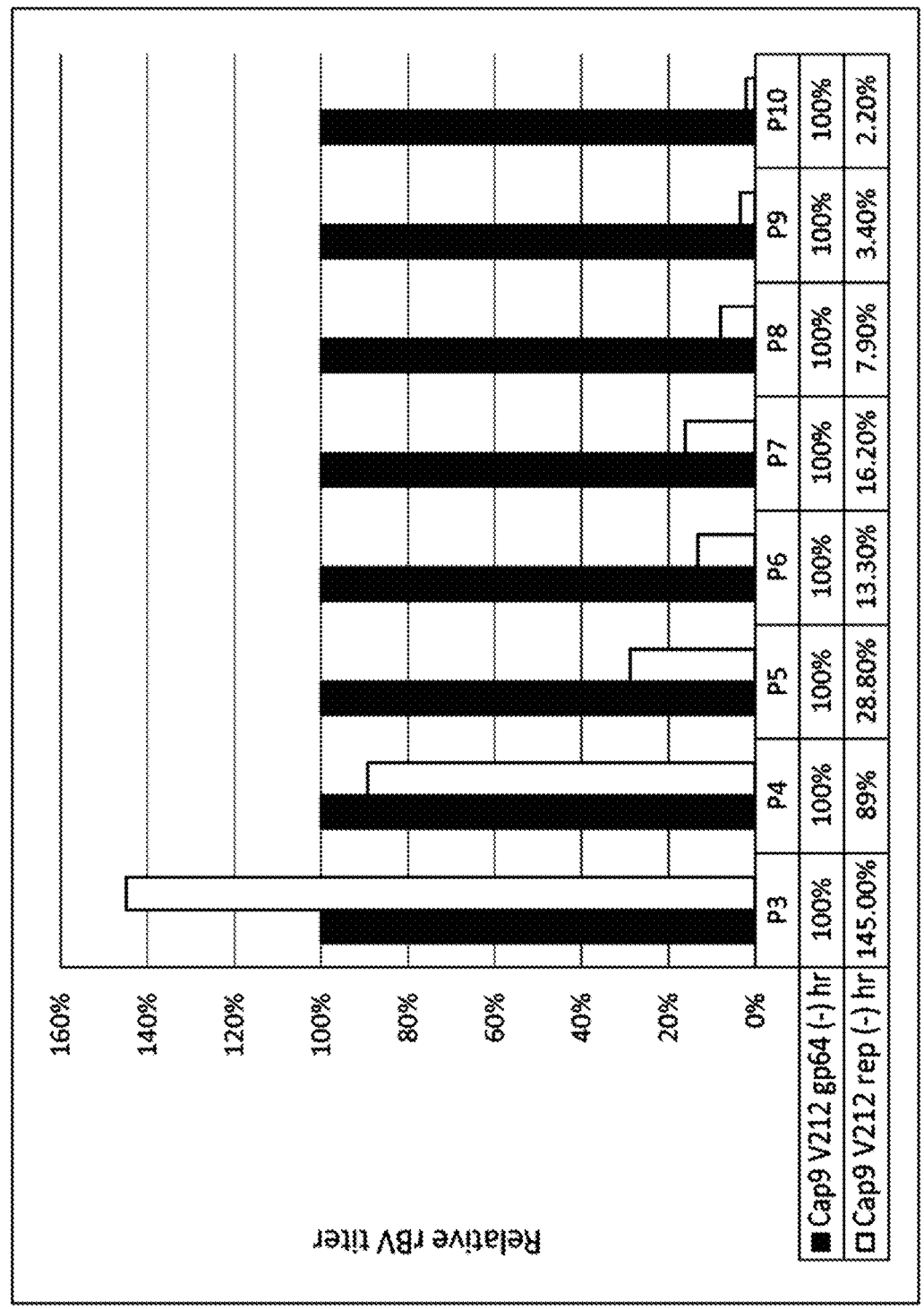
Figure 9F:
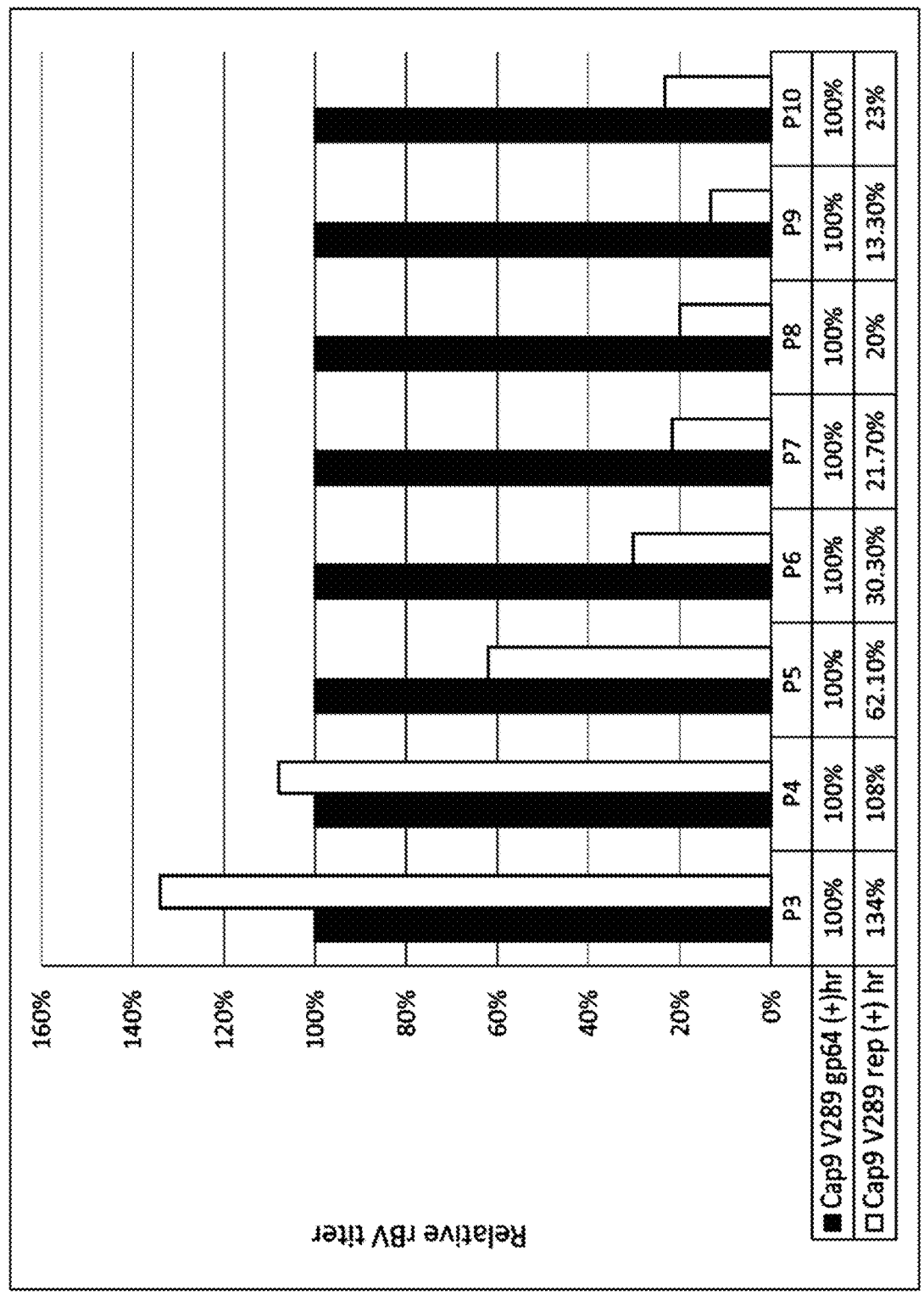
Figure 9G:
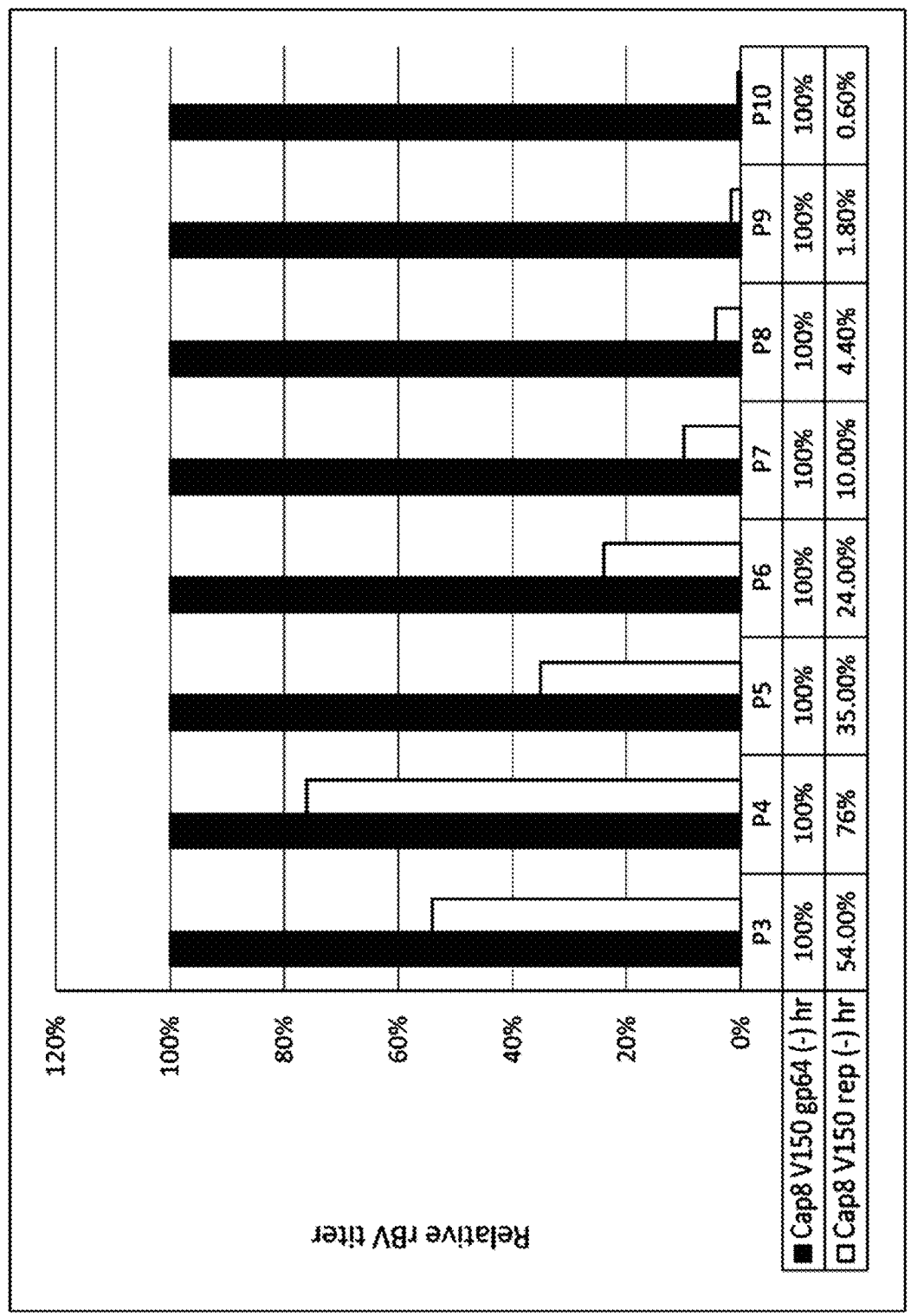

Recombinant baculoviruses carrying Cap1-Rep (FIG. 5), Cap6-Rep (FIG. 4), Cap9-Rep (FIG. 3), and Cap8-Rep (FIG. 2) were selected for these experiments. For each passage, the total baculovirus pfu was determined with the gp64 primers, and set to 100%. The specific baculovirus for each passage was determined using the Rep primers set as percentage of total baculovirus. The results are shown in FIG. 9A-H for recombinant baculovirus (rBV) titers with or without the hr2 sequence. FIG. 9A illustrates rBV titers determined with gp64 and rep2 qPCR primers in cells harboring rBV-inCap1-inRep (Cap1 VI88) expressing AAV1 capsid and AAV2 rep genes without the hr2 sequence. FIG. 9B illustrates rBV titers determined with gp64 and rep2 qPCR primers in cells harboring rBV-inCap1-inRep-hr2 (Cap1 V291 expressing AAV1 capsid and AAV2 rep genes with the hr2 sequence). FIG. 9C illustrates rBV titers determined with gp64 and rep2 qPCR primers in cells harboring rBV expressing AAV6 capsid and AAV2 rep genes without the hr2 sequence. FIG. 9D illustrates rBV titers determined with gp64 and rep2 qPCR primers in cells harboring rBV-inCap6-inRep (Cap6 V195) expressing AAV6 capsid and AAV2 rep genes with the hr2 sequence. FIG. 9E illustrates rBV titers determined with gp64 and rep2 qPCR primers in cells harboring rBV-inCap9-inRep (Cap9 V212) expressing AAV9 capsid and AAV2 rep genes without hr2 sequence. FIG. 9F illustrates rBV titers determined with gp64 and rep2 qPCR primers in cells harboring rBV-inCap9-inRep-hr2 (Cap9 V289) expressing AAV9 capsid and AAV2 rep genes with hr2 sequence. FIG. 9G illustrates rBV titers determined with gp64 and rep2 qPCR primers in cells harboring rBV-Cap8-inRep (Cap8 V150) expressing AAV8 capsid and AAV2 rep genes without hr2 sequence. FIG. 9H illustrates rBV titers determined with gp64 and rep2 qPCR primers in cells harboring rBV-inCap8-inRep-hr2 (Cap8 V288) expressing AAV8 capsid and AAV2 rep genes with hr2 sequence. rBVs were produced and passaged in Sf9 cells (FIG. 9A-D), Tni pro cells (FIG. 9E-F), and E4a cells (FIG. 9G-H). The data indicate that specific baculovirus titer decreased with increasing number of passages when the baculovirus did not contain an hr2 sequence (FIG. 9A, FIG. 9C, FIG. 9E, and FIG. 9G), whereas there was a smaller decrease in specific baculovirus titer when the baculovirus contained the hr2 sequence near the rep expression cassette (FIG. 9B, FIG. 9D, FIG. 9F, and FIG. 9H). These changes held true regardless of whether SF9 (FIG. 9A-9D). Tni Pro (FIG. 9E-F), or E4a cells (FIG. 9G-H) were the host cells. By passage P10, baculovirus with AAV Cap1 or AAV Cap 6 were below 10% of total rBV titer when the vectors contained no hr (FIG. 9A, FIG. 9C, FIG. 9E, and FIG. 9G), but baculovirus with AAV Cap1 or AAV Cap 6 were about 20% of total rBV titer when the vectors contained hr2 (FIG. 9B, FIG. 9D, FIG. 9F, FIG. 9H).

Example 9

This example illustrates that an hr sequence enhances AAV productivity of recombinant baculoviruses (rBV) containing the AAV rep and cap genes.

Figure 10B:
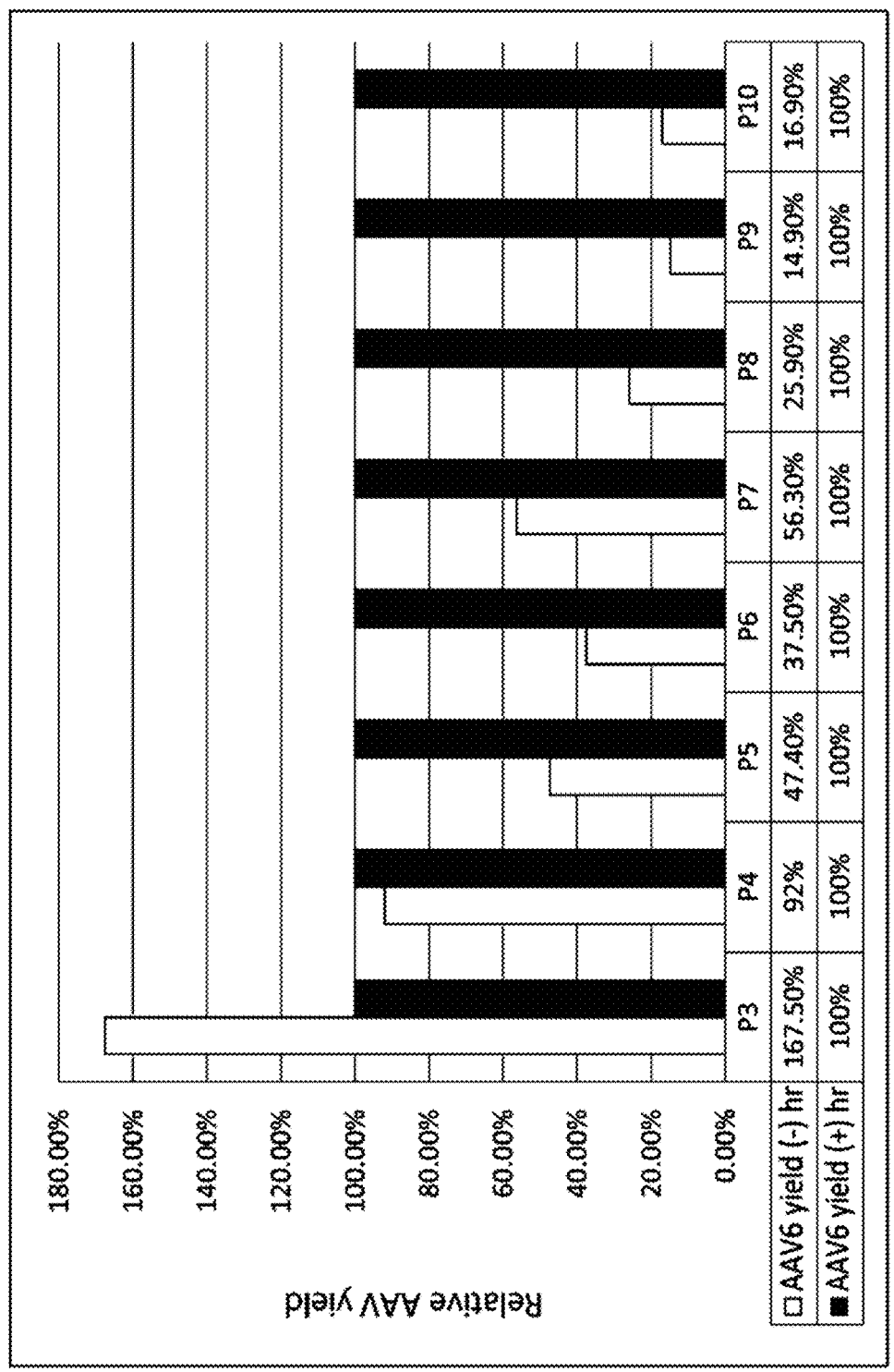
Figure 10D:
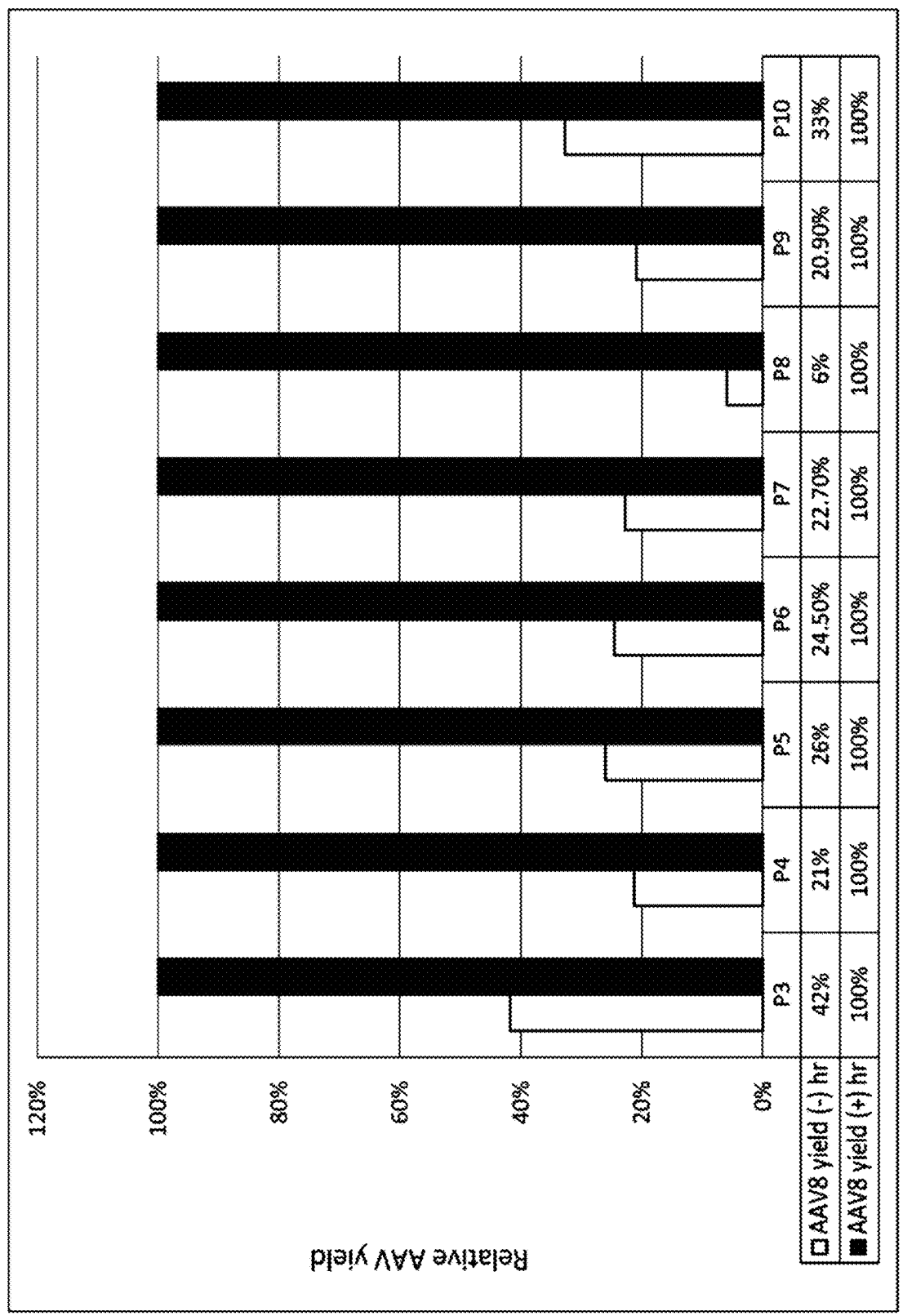
Figure 10E:
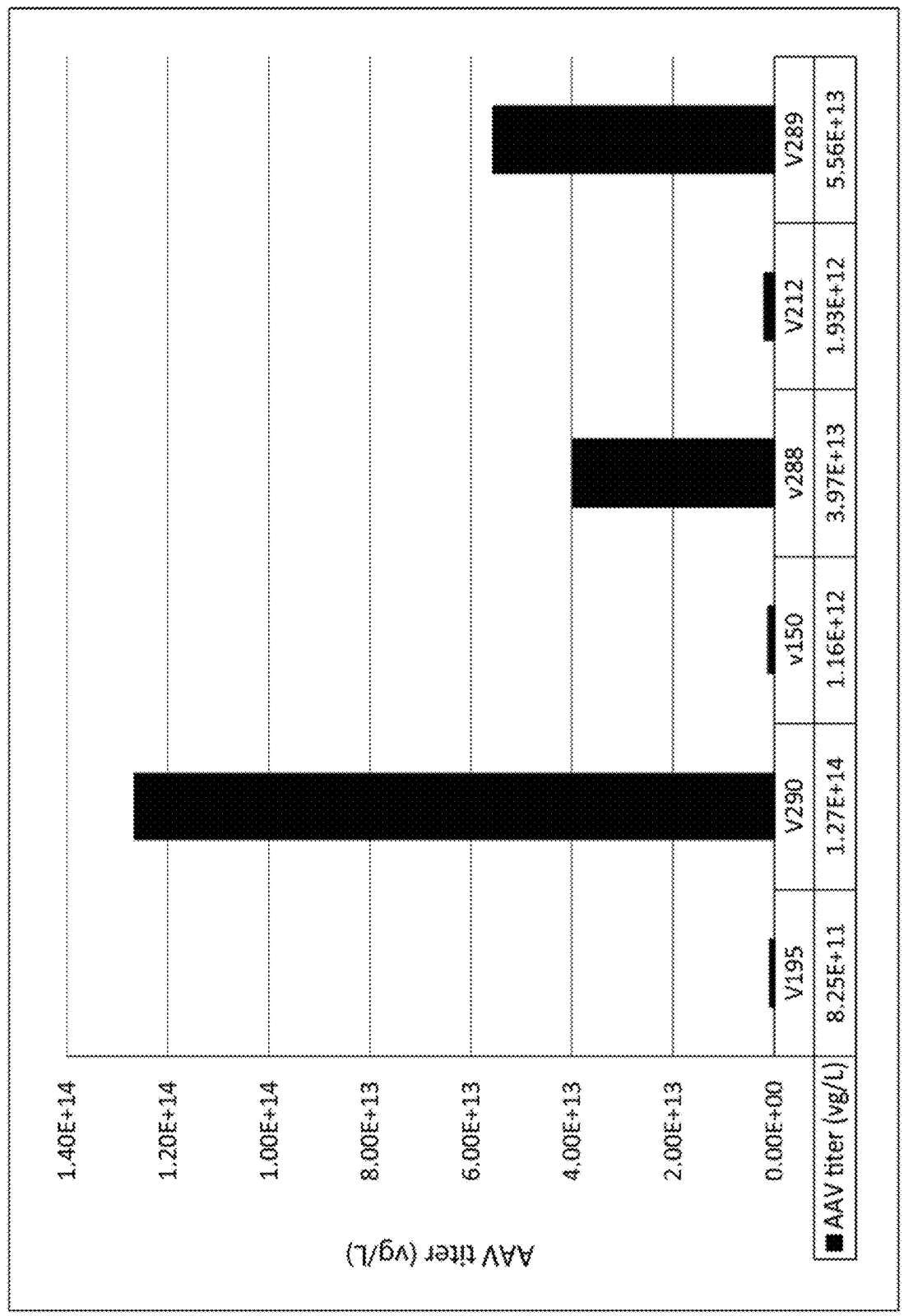

In these experiments, the rBVs with or without the hr sequence from passage 3 to passage 10 were used to co-infect Sf9, Tni Pro, and E4a cell lines with the rBV containing GFP to produce AAV vectors. After three days of co-infection, the cell pellets were harvested and AAV production yields were determined. As shown in FIG. 10A-D, the production yield of AAV1 in Sf9 cells (FIG. 10A), AAV6 in Sf9 cells (FIG. 10B), AAV9 in Tni pro cells (FIG. 10C) and AAV8 in E4a cells (FIG. 10D) was maintained over passages 3-10 when the baculovirus vector included an hr2 sequence. In contrast, production yield of AAV1, AAV6, AAV9, and AAV8 declined dramatically over passages 3-10 in the absence of hr2 in the rBV. To further confirm this observation, S9 cells were co-infected with passage 10 rBVs with hr2 (V290, V288, and V289) or without hr2 (V195, V150, and V212) sequence to produce AAV6 (V195 and V290), AAV8 (V150 and V288), and AAV9 (V212 and V289) vectors. The results show substantially higher AAV production yields from S9 cells infected with rBV containing hr2 than those infected with rBV without hr2 sequence (FIG. 10E) (compare hr+ rBVs V290, V288 and V289, to hr rBVs V195, V150 and V212).

Example 10

This example illustrates that AAV rep and cap expression directly correlates with rBV stability through multiple passages.

Figure 11A:
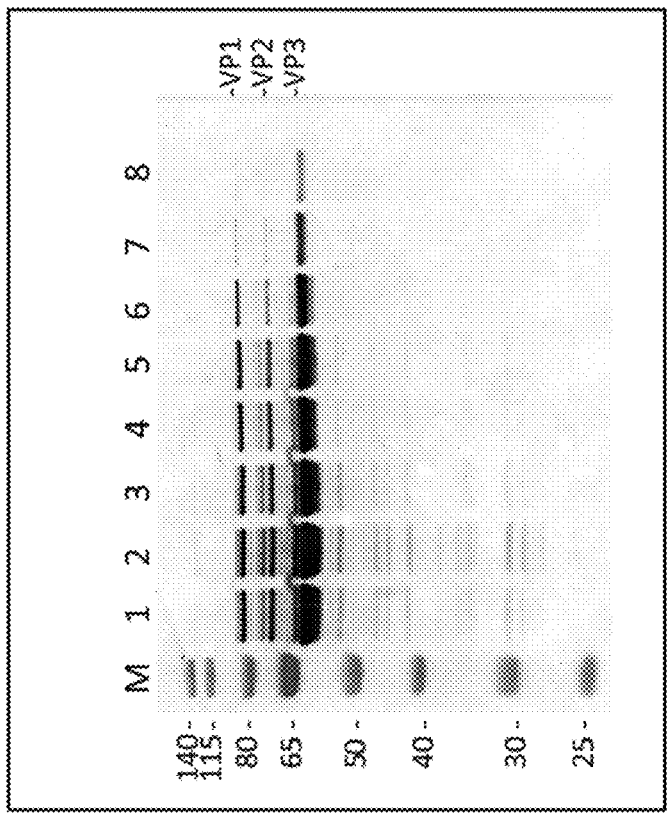
FIG. 11A-B illustrates Western blot expression of AAV capsid proteins in cells infected with recombinant baculoviruses with and without hr2 sequences.
Figure 11B:
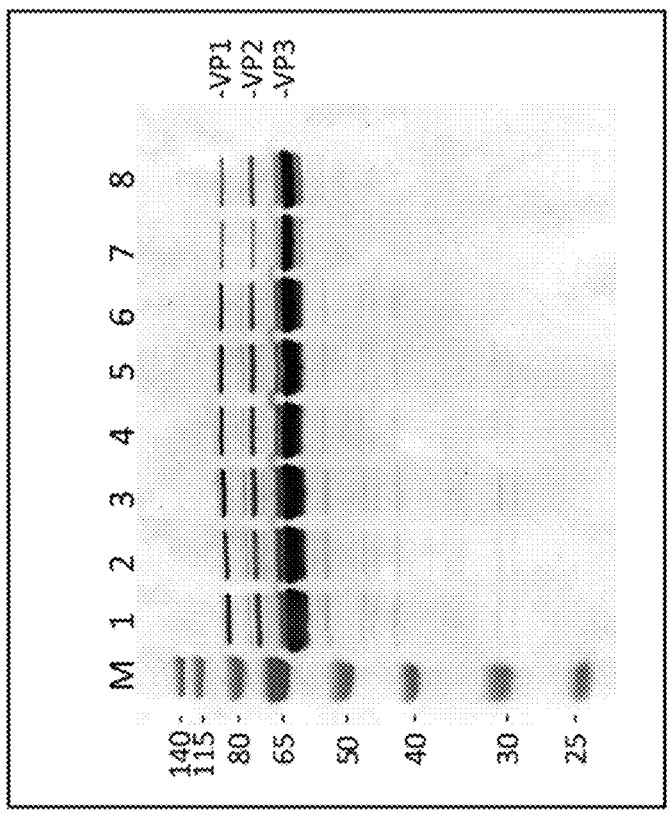

In these experiments, Western blots were performed to determine the expression level of rep and cap proteins. FIG. 11A-B illustrate the expression of AAV6 capsid proteins VP1, VP2, and VP3 after infection of Sf9 cells with recombinant baculoviruses rBV-inCap6-inRep (V195) without hr2 sequence (FIG. 11A) and rBV-inCap6-inRep-hr2 (V290) with hr2 sequence (FIG. 11B) from passage 3 to passage 10 respectively. M, protein size markers; lanes 1 to 8, cell lysates prepared from Sf9 cells infected with rBVs from passages 3 to 10.

Figure 12A:
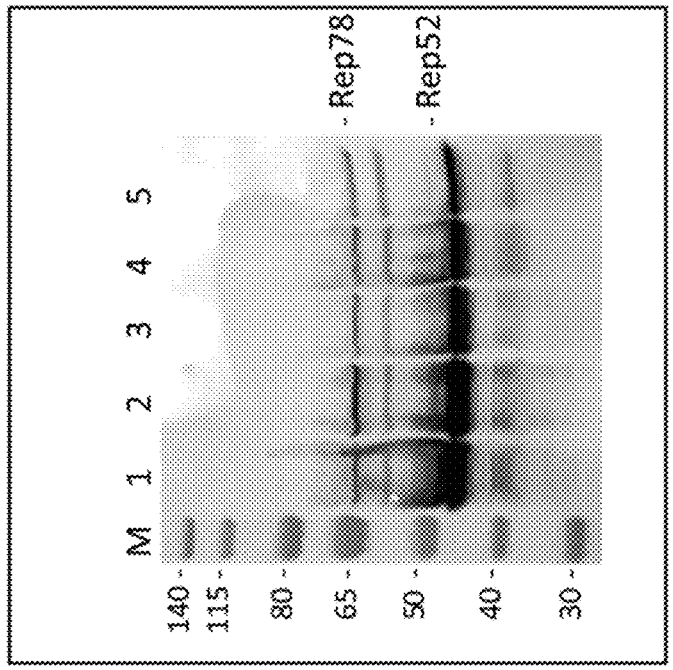
FIG. 12 A-B illustrates Western blot expression of AAV rep proteins in cells infected with recombinant baculoviruses with and without hr2 sequences.
Figure 12B:
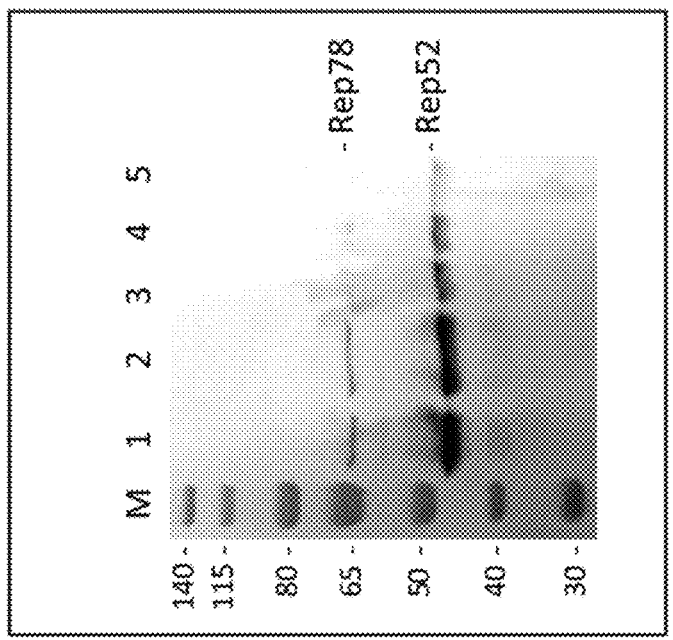

FIG. 12A-B illustrate the expression of AAV2 rep proteins REP78 and REP52 after infection of Sf9 cells with recombinant baculoviruses rBV-inCap8-inRep (V150) without hr2 sequence (FIG. 12A) and rBV-inCap8-inRep-hr2 (V288) with hr2 sequence (FIG. 12B). M, protein size markers; lanes 1-5, cell lysates prepared from Sf9 cells infected with rBVs from passages 6 to 10. The results in FIG. 11 and FIG. 12 indicate that rBVs with an hr sequence express higher levels of rep and cap proteins throughout multiple passages, including later passages, compared to rBVs lacking an hr sequence.

All cited references are incorporated by reference, each in its entirety. Applicant reserves the right to challenge any conclusions presented by the authors of any reference.

What is claimed is:

1. A baculovirus vector for adeno-associated virus (AAV) production, comprising:
   an AAV Cap expression cassette;
   an AAV Rep expression cassette; and
   a baculovirus homologous region 2 (hr2) located up to about 4 kb from a start codon of an AAV expression cassette, wherein the vector has no Rep binding element (RBE) sequence, no inverted terminal region (ITR) containing an RBE sequence, and no promoter containing an RBE sequence.

2. The vector in accordance with claim 1, wherein the hr2 region is between the Rep expression cassette and the Cap expression cassette, and wherein the Rep expression cassette and the Cap expression cassette are in a head to head (5' to 5') orientation.

3. An insect cell line comprising cells comprising a vector in accordance claim 1.

4. The insect cell line in accordance with claim 3, wherein the cells further comprise a second vector, said second vector comprising a transgene flanked by AAV ITRs.

5. A method of growing baculovirus in vitro, comprising: providing a culture of insect cells in accordance with claim 3; and incubating the cells.

6. The method in accordance with claim 5, wherein the incubating the cells comprises passaging the cells, and wherein AAV production yield at passage 7 is at least 2-fold greater compared to a control insect cell line comprising a baculovirus vector comprising an AAV Cap expression cassette and an AAV Rep expression cassette but no baculovirus hr.

7. The method in accordance with claim 5, wherein the titer at passage 7 of baculovirus comprising the AAV Cap expression cassette is greater than 21.5% of total baculovirus titer.

8. A method of growing AAV in vitro, comprising:
   providing a culture of insect cells;
   infecting or transfecting the insect cells with a baculovirus vector in accordance with claim 1; and
   incubating the cells.

9. The method in accordance with claim 8, wherein the yield at P7 of AAV from the insect cells is at least 50% greater than the yield at P7 of AAV from insect cells comprising a baculovirus vector without the hr.

10. The method in accordance with claim 8, wherein the yield at P7 of AAV from cells comprising the baculovirus hr is at least 20% greater than the yield of AAV from cells comprising a baculovirus vector without the hr.

11. The method in accordance with claim 8, wherein the baculovirus vector is exclusive of a Rep binding element (RBE).

12. A method of producing AAV in vitro, comprising growing an insect cell culture comprising a vector in accordance with claim 1, and a vector comprising a transgene flanked by AAV ITRs.

* * * * *